(12) United States Patent
Rahn et al.

(10) Patent No.: US 7,933,010 B2
(45) Date of Patent: Apr. 26, 2011

(54) DEPTH OF FIELD EXTENSION FOR OPTICAL TOMOGRAPHY

(76) Inventors: J. Richard Rahn, Sammamish, WA (US); John W. Hayenga, Redmond, WA (US)

(*) Notice: Subject to any disclaimer, the term of this patent is extended or adjusted under 35 U.S.C. 154(b) by 0 days.

(21) Appl. No.: 12/862,553

(22) Filed: Aug. 24, 2010

(65) Prior Publication Data

US 2010/0321786 A1 Dec. 23, 2010

Related U.S. Application Data

(62) Division of application No. 11/876,658, filed on Oct. 22, 2007, now Pat. No. 7,787,112.

(51) Int. Cl.
*G01J 1/00* (2006.01)
(52) U.S. Cl. ................................. 356/213; 356/234
(58) Field of Classification Search .......... 356/213–236; 250/455.11–461.2; 382/131–134; 435/447–448; 600/309–310; 378/6–11, 21–28; 702/19, 702/21, 28–29; 377/10–12; 73/53.01, 61.69–61.72
See application file for complete search history.

(56) References Cited

U.S. PATENT DOCUMENTS

| | | | |
|---|---|---|---|
| 3,470,373 A | 9/1969 | Brewer | |
| 3,497,690 A | 2/1970 | Wheeless, Jr. | |
| 3,598,471 A | 8/1971 | Baldwin | |
| 3,657,537 A | 4/1972 | Wheeless, Jr. | |
| 3,748,468 A | 7/1973 | Hartman | |
| 3,833,762 A | 9/1974 | Gudmundsen | |
| 3,960,449 A | 6/1976 | Carlton | |
| 3,999,047 A | 12/1976 | Green | |
| 4,081,277 A | 3/1978 | Brault et al. | |
| 4,175,860 A | 11/1979 | Baucus | |
| 4,183,623 A | 1/1980 | Haines | |
| 4,200,353 A | 4/1980 | Hoffman | |
| 4,293,221 A | 10/1981 | Kay | |
| 4,360,885 A | 11/1982 | Edgar | |
| 4,702,598 A | 10/1987 | Bohmer | |
| 4,714,345 A | 12/1987 | Schrader | |
| 4,858,128 A | 8/1989 | Nowak | |

(Continued)

FOREIGN PATENT DOCUMENTS

JP 02085747 A * 3/1990

(Continued)

OTHER PUBLICATIONS

Fauver et al., "Three-dimensional image of single isolated cell nuclei using optical projection tomography," Optics Express, May 30, 2005/vol. 13 No. 11/4210-4223.

(Continued)

*Primary Examiner* — Gregory J Toatley
*Assistant Examiner* — Tri T Ton
(74) *Attorney, Agent, or Firm* — George A. Leone; Citadel Patent Law

(57) ABSTRACT

An optical tomography system for viewing an object of interest includes a microcapillary tube viewing area for positioning the object of interest in an optical path including a detector. A motor is located to attach to and rotate a microcapillary tube. A device is arranged for transmitting broadband light having wavelengths between 550 nm and 620 nm into the microcapillary tube viewing area. A hyperchromatic lens is located to receive light transmitted through the microcapillary tube viewing area. A tube lens is located to focus light rays transmitted through the hyperchromatic lens, such that light rays from multiple object planes in the microcapillary tube viewing area simultaneously focus on the at least one detector.

5 Claims, 26 Drawing Sheets

U.S. PATENT DOCUMENTS

| | | |
|---|---|---|
| 4,873,653 A | 10/1989 | Grosskopf |
| 4,891,829 A | 1/1990 | Deckman |
| 5,141,609 A | 8/1992 | Sweedler |
| 5,148,502 A | 9/1992 | Tsujiuchi |
| 5,281,517 A | 1/1994 | Bacus |
| 5,308,990 A | 5/1994 | Takahashi |
| 5,312,535 A | 5/1994 | Waska |
| 5,321,501 A | 6/1994 | Swanson |
| 5,333,164 A | 7/1994 | Tam |
| 5,390,226 A | 2/1995 | Tam |
| 5,402,460 A | 3/1995 | Johnson |
| 5,428,447 A | 6/1995 | Toida |
| 5,539,800 A | 7/1996 | Katsevich |
| 5,548,395 A | 8/1996 | Kosaka |
| 5,552,605 A | 9/1996 | Arata |
| 5,644,388 A | 7/1997 | Maekawa et al. |
| 5,668,887 A | 9/1997 | Parker |
| 5,673,300 A | 9/1997 | Reckwerdt |
| 5,680,484 A | 10/1997 | Ohyama |
| 5,710,429 A | 1/1998 | Alfano |
| 5,741,411 A | 4/1998 | Yeung |
| 5,760,901 A | 6/1998 | Hill |
| 5,760,951 A | 6/1998 | Dixon |
| 5,784,352 A | 7/1998 | Swanson et al. |
| 5,828,408 A | 10/1998 | Mottin |
| 5,831,723 A | 11/1998 | Kubota |
| 5,848,123 A | 12/1998 | Strommer |
| 5,878,103 A | 3/1999 | Sauer |
| 5,880,838 A | 3/1999 | Marx |
| 5,909,476 A | 6/1999 | Cheng |
| 5,915,048 A | 6/1999 | Hill |
| 5,956,355 A | 9/1999 | Swanson et al. |
| 5,987,158 A | 11/1999 | Meyer |
| 6,005,617 A | 12/1999 | Shimamoto |
| 6,026,174 A | 2/2000 | Palcic |
| 6,037,579 A | 3/2000 | Chan et al. |
| 6,038,067 A | 3/2000 | George |
| 6,047,080 A | 4/2000 | Chen |
| 6,072,624 A | 6/2000 | Dixon |
| 6,078,681 A | 6/2000 | Silver |
| 6,091,983 A | 7/2000 | Alfano |
| 6,111,645 A | 8/2000 | Tearney et al. |
| 6,130,958 A | 10/2000 | Rohler |
| 6,134,003 A | 10/2000 | Tearney et al. |
| 6,160,826 A | 12/2000 | Swanson et al. |
| 6,165,734 A | 12/2000 | Garini |
| 6,192,144 B1 | 2/2001 | Holz |
| 6,201,628 B1 | 3/2001 | Basiji |
| 6,211,955 B1 | 4/2001 | Basiji |
| 6,215,587 B1 | 4/2001 | Alfano |
| 6,239,871 B1 | 5/2001 | Gilby |
| 6,248,988 B1 | 6/2001 | Krantz |
| 6,249,341 B1 | 6/2001 | Basiji |
| 6,251,586 B1 | 6/2001 | Mulshine |
| 6,251,615 B1 | 6/2001 | Oberhardt |
| 6,252,979 B1 | 6/2001 | Lee |
| 6,282,011 B1 | 8/2001 | Tearney et al. |
| 6,291,824 B1 | 9/2001 | Battarbee |
| 6,312,914 B1 | 11/2001 | Kardos |
| 6,365,367 B1 | 4/2002 | Friedman et al. |
| 6,388,809 B1 | 5/2002 | MacAulay |
| 6,421,164 B2 | 7/2002 | Tearney et al. |
| 6,452,179 B1 | 9/2002 | Coates |
| 6,473,176 B2 | 10/2002 | Basiji |
| 6,485,413 B1 | 11/2002 | Boppart et al. |
| 6,501,551 B1 | 12/2002 | Tearney et al. |
| 6,519,355 B2 | 2/2003 | Nelson |
| 6,522,775 B2 | 2/2003 | Nelson |
| 6,529,614 B1 | 3/2003 | Chao |
| 6,540,895 B1 | 4/2003 | Spence et al. |
| 6,564,087 B1 | 5/2003 | Pitris et al. |
| 6,591,003 B2 | 7/2003 | Chu |
| 6,608,682 B2 | 8/2003 | Ortyn et al. |
| 6,624,930 B1 | 9/2003 | Danner et al. |
| 6,636,623 B2 | 10/2003 | Nelson |
| 6,640,014 B1 | 10/2003 | Price |
| 6,697,508 B2 | 2/2004 | Nelson |
| 6,725,073 B1 | 4/2004 | Motamedi et al. |
| 6,741,730 B2 | 5/2004 | Rahn |
| 6,770,893 B2 | 8/2004 | Nelson |
| 6,775,399 B1 | 8/2004 | Jiang |
| 6,842,297 B2 | 1/2005 | Dowski, Jr. |
| 6,850,587 B1 | 2/2005 | Karimi |
| 6,868,177 B1 | 3/2005 | Sitton et al. |
| 6,944,322 B2 | 9/2005 | Johnson |
| 6,975,400 B2 | 12/2005 | Ortyn et al. |
| 6,991,738 B1 | 1/2006 | Fauver |
| 7,003,143 B1 | 2/2006 | Hewitt |
| 7,197,355 B2 | 3/2007 | Nelson |
| 7,218,393 B2 | 5/2007 | Sharpe et al. |
| 7,224,540 B2 | 5/2007 | Olmstead et al. |
| 7,260,253 B2 | 8/2007 | Rahn |
| 7,274,809 B2 | 9/2007 | MacUalay et al. |
| 2001/0012069 A1 | 8/2001 | Derndinger |
| 2002/0122167 A1 | 9/2002 | Riley et al. |
| 2002/0161534 A1 | 10/2002 | Adler |
| 2003/0063384 A1 | 4/2003 | Dowski, Jr. |
| 2003/0199758 A1 | 10/2003 | Nelson |
| 2003/0222197 A1 | 12/2003 | Reese |
| 2004/0001618 A1 | 1/2004 | Johnson |
| 2004/0008515 A1 | 1/2004 | Brown |
| 2004/0076319 A1 | 4/2004 | Fauver |
| 2004/0197839 A1 | 10/2004 | Daniely et al. |
| 2005/0006595 A1 | 1/2005 | Goodwin |
| 2005/0010108 A1 | 1/2005 | Rahn |
| 2005/0085708 A1 | 4/2005 | Fauver |
| 2005/0085721 A1 | 4/2005 | Fauver |
| 2006/0023219 A1 | 2/2006 | Meyer |
| 2006/0066837 A1 | 3/2006 | Ortyn et al. |
| 2006/0068371 A1 | 3/2006 | Ortyn et al. |
| 2006/0093200 A1 | 5/2006 | Sharpe et al. |
| 2006/0096358 A1 | 5/2006 | Fauver |
| 2006/0099707 A1 | 5/2006 | Nelson |
| 2006/0171041 A1 | 8/2006 | Olmstead et al. |
| 2006/0183220 A1 | 8/2006 | Nelson |
| 2006/0188869 A1 | 8/2006 | Zeskind et al. |
| 2006/0204071 A1 | 9/2006 | Ortyn et al. |
| 2007/0071357 A1 | 3/2007 | Rahn |
| 2007/0146873 A1 | 6/2007 | Ortyn et al. |
| 2007/0215528 A1 | 9/2007 | Hayenga |
| 2007/0258122 A1 | 11/2007 | Chamgoulov et al. |

FOREIGN PATENT DOCUMENTS

| | | | |
|---|---|---|---|
| JP | 10260131 A | * | 9/1998 |
| JP | 2000121550 A | * | 4/2000 |
| WO | WO0111341 A2 | * | 2/2001 |
| WO | WO0218537 A2 | * | 3/2002 |
| WO | WO0235474 A1 | * | 5/2002 |
| WO | WO02095476 A2 | * | 11/2002 |
| WO | WO03003057 A2 | * | 1/2003 |

OTHER PUBLICATIONS

Fauver et al.,"Development of Micro-Optical Projection Tomography for 3D Analysis of Single Cells," Image Acquisition and Processing XI. Edited by Conchello, Jose-Angel; Cogswell, Carol J.; Wilson, Tony. Proceedings of the SPIE, vol. 5324, pp. 171-181 (2004).

Kikuchi, S. et al., "Three-dimensional computed tomography for optical microscopes," Optics Communications 107 (1994) 432-444.

Kikuchi, S. et al., "Three-dimensional microscope computed tomography based on general Radon transform for optical imaging systems," Optics Communication 123 (1996) 725-733.

Matula, P. et al. "Precise 3D image alignment in micro-axial tomography," Journal of Microscopy, vol. 209, Pt. 2 (Feb. 2003) pp. 126-142.

Ong, SH, Development of an imaging flow cytometer. Anal Quant Cytol Histol 9(5)pp. 375-82, 1987.

Gilbert, P, "Iterative Methods for the Three dimensional Reconstruction of an Object from Projections," Journal of Theoretical Biology 36 pp. 105-117, 1972.

Oppenheim, BE, More Accurate Algorithms for Iterative 3 dimensional Reconstruction, IEEE Transactions on Nuclear Science NS-21pp. 72-77, 1974.

Singer, JR, Grunbaum, FA, Kohn, P, and Zubelli, JP, "Image Reconstruction of the Interior of Bodies that Diffuse Radiation," Science 248(4958)pp. 990-993, 1990.

Mueller, K and Yage, R, "Rapid 3-D Cone-beam Reconstruction with the Simultaneous Algebraic Reconstruction Technique (SART) Using 2-D Texture Mapping Hardware", IEEE Transactions on Medical imaging 19(12)pp. 1227-1237, 2001.

Bellman, SH, Bender, R, Gordon, R, and Rowe, JE, "ART is Science being a Defense of Algebraic Reconstruction Techniques for Three dimensional Electron Microscopy," Journal of Theoretical Biology 32pp. 205-216, 1971.

Manglos,SH, Jaszcak, RJ, and Floyd, CE, "Maximum Likelihood Reconstruction for Cone Beam SPECT: Development and Initial Tests," Physics in Medicine and Biology 34(12)pp. 1947-1957,1989, #1382.

Manglos,SH, Gagne, GM, Krol A, Thomas, FD, and Narayanaswamy, R, "Transmission Maximum-likelihood Reconstruction with Ordered Subsets for Cone Beam CT", Physics in Medicine and Biology 40(7)pp. 1225-1241, 1995, #4389.

Hampel, U and Freyer, R, "Fast Image Reconstruction for Optical Absorption Tomography in Media with Radially Symmetric Boundaries", Medical Physics 25 (1)pp. 92-101, 1998.

Jiang, H, Paulsen, KD, and Osterberg, UL, "Frequency-domain Near-infrared Photo Diffusion Imaging: Initial Evaluation in Multitarget Tissuelike Phantoms", Medical Physics 25(2)pp. 183-193,1998.

Herman, G, Image Reconstruction from Projections: The Fundamentals of Computerized Tomography, Academic Press, New York, 1980.

Paulsen, KD and Jiang, H, "Spatially Varying Optical Property Reconstruction Using a Finite Element Diffusion Equation Approximation", Medical Physics 22(691-701) 1995.

Shapiro, HM, Practical Flow Cytometry, 3rd ed., Wiley-Liss, 1995.

HJ Tiziani, and MI Uhde, Three-dimensional analysis by a microlens array confocal arrangements (Applied Optics 33, 567 [1994]).

Bentley, MD, Ortiz, MC, Ritman, EL, and Romero, JC, The Use of Microcomputed Tomography to Study Microvasculature in Small Rodents, American Journal of Physiology (Regulatory Integrative Comp Physiol) 282 (R1267-R1279) 2002.

Cheng, PC, Lin, TH, Wang, G, Shinozaki, DM, Kim, HG, and Newberry, SP, "Review on the Development of Cone-beam X-ray Microtomography", Proceedings of the X-ray Optics and Microanalysis 1992, Institute of Physics Ser. No. 130, Kenway, PB, et al. (eds.), Manchester, UK, Aug. 31-Sep. 4, 1992, pp. 559-566.

Defrise, M, Clack, R, and Townsend, DW, "Image Reconstruction from Truncated, Two-dimensional, Parallel Projections", Inverse Problems 11(287-313) 1995.

Defrise, M, Noo, F, and Kudo, H, "A Solution to the Long-object Problem in Helical Cone-beam Tomography", Physics in Medicine and Biology 45(623-43) 2000.

Endo, M, Tsunoo, T, Nakamori, N, and Yoshida, K, "Effect of Scattered Radiation on Image Noise in Cone Beam CT", Medical Physics 28(4) (469-74) 2001.

Jorgensen, SM, Demirkaya, 0, and Ritman, EL, "Three Dimensional Imaging of Vasculature and Parenchyma in Intact Rodent Organs with X-ray Micro-CT", Am. J. Physiology 275(Heart Circ. Physiol. 44) pp. H1103-H1114, 1998.

Kinney JH Johnson, QC, Saroyan, RA, Nichols, MC, Bonse, U, Nusshardt, R, and Pahl, R, "Energy-modulated X-ray .Microtomography", Rev. Sci. Instrum. 59(1)pp. 196-197, 1988.

Kinney,JH, and Nichols, MC, "X-ray Tomographic Microscopy (XTM) Using Synchrotron Ratiation", Annu. Rev. Mater. Sci. 22pp. 121-152, 1992.

Taguchi, K and Aradate, H, "Algorithm for Image Reconstruction in Multi-slice Helical CT", Medical Physics 25(4) pp. 550-561, 1998.

Yu, DF, Fessler, JA, and Ficaro, EP, "Maximum-Likelihood Transmission Image Reconstruction for Overlapping Transmission Beams", IEEE Transactions on Medical Imaging 19(11)pp. 1094-1105, 2000.

Sharpe, J, Ahlgren, U et al., "Optical Projection Tomography as a Tool for 3D Microscopy and Gene Expression Studies," Science, vol. 296, pp. 541-545, Apr. 19, 2002.

Sharpe, J, review, "Optical Projection Tomography as a New Tool for Studying Embryo Anatomy," J. Anat. (2003), pp. 175-181.

RH Anderson, "Close-up imaging of documents and displays with lens arrays," AppliedOptics 18, 477 (1979).

A. Klug, "Image analysis and reconstruction in the electron microscopy of biological macromolecules," Chem. Scripta, vol. 14, p. 245 (1978).

T. C. Wedberg and J.J. Stamnes, "Recent results in optical diffraction microtomography," Meas. Sci. Technol., vol. 7, p. 414 (1996).

Y. Xu et al., "Three-dimensional diffuse optical tomography of bones and joints," J. Biomed. Optics, vol. 7, p. 88 (2002).

Smolinska and Dawidowicz, "Extraction of common or different part from optical images," Institute of Physics, Warsaw Technical University, 222-223.

Pawley, JB, Handbook of Biological Confocal Microscopy, Plenum Press, NY 479-490 (1995).

George, JS et al., "Virtual Pinhole Confocal Microscope," Physics Division Progress Report, www.lanl.gov/p/pdfs/papp_pinhole.pdf, (1999-2000).

Sara Abragamsson, Satoru Usawa and Mats Gustafsson, A new approach to extended focus for high-speed, high-resolution biological microscopy, Proc. of SPIE vol. 60900, N1-N8, (2006).

Rainer Leitgeb, Martin Villiger, Adrian Bachmann, Lukas Steinmann, and Theo Lasser, Extended focus depth for Fourier domain optical coherence microscopy, Optics Letters, Doc. ID 69650, Jun. 1, 2006.

Harold R. Suiter, Apodization for Obstructed Apertures, home. digitalexp.com., 2001.

Sara Bradburn, Wade Thomas Cathey, and Edward R. Dowski, Jr., Realizations of Focus Invariance in Optical/Digital Systems with Wavefront Coding, Applied Optics, vol. 36, Issue 35, pp., 9157-9166 (1997).

P. Edelmann, A. Esa, H. Bomfleth, R. Heintzmann, M. Hausmann, C. Cremer, Correlation of chromatic shifts and focal depth in Spectral Precision Distance Microscopy measured by Micro Axial Tomography, Optical Biopsies and Microscopic Techniques III, Sep. 1999, SPIE vol. 3568, pp. 89-95.

Pierre M. Lane, Robert P. Elliott A and Calum E. MacAulay, Confocal Microendoscopy with Chromatic Sectioning, Spectral Imaging: Instrumentation, Applications, and Analysis II, Proc. of SPIE vol. 4959 pp. 23-26 (2003).

C. J. R. J R Sheppard & P. Torok, Effects of specimen refractive index on confocal imaging, Journal of Microscopy, vol. 185, Pt. 3, Mar. 1997, pp. 366-374.

Daniel L. Marks, Ronald A. Stack, and David J. Brady, Three-dimensional tomography using a cubic-phase plate extended depth-of-field system, Optics Letters, vol. 24, No. 4, Feb. 15, 1999.

A. Miks, J. Novak, P. Novak, Theory of hyperchromats with linear longitudinal chromatic, aberration, Proc. of SPIE, vol. 5945, pp. 59450, Y1-Y8, (2005).

Mikula, G. et al., Imaging with extended focal depth by means of lenses with radial and angular modulation, Optics Express, vol. 15, No. 15, Jul. 23, pp. 9184-9193 (2007).

Porras, R., et al., Wavefront coding technology in the optical design of astronomical instruments, 5th Iberoamerican Meeting on Optics and 8th Latin American Meeting on Optics, Lasers, and Their Applications, edited by A. Marcano 0., J. L. Paz, Proc. of SPIE vol. 5622, pp. 796-800 (2004).

Somayaji, M. et al., Enhancing form factor and light collection of multiplex imaging systems by using a cubic phase mask, Applied Optics, vol. 45, No. 13, May 1, pp. 2911-2923, (2006).

Tucker, S.C. et al., Extended depth of field and aberration control for inexpensive digital microscope systems, Optics Express, vol. 4, No. 11, May 24, pp. 467-474 (1999).

Xu, Y. et al, Ultra long high resolution beam by multi-zone rotationally symmetrical complex pupil filter, Optics Express, vol. 15, No. 10, May 10, pp. 6409-6413 (2007).

Long, J.C. et al., Tube Lens Focal Length, Nikon Microscopy U: Interactive Java Tutorials, http://www.microscopy.com (2007).

Forster, B. et al., Complex Wavelets for Extended Depth-of-Field: A New Method for the Fusion of Multichannel Microscopy Images, Microscopy Research and Technique 65:33-42 (2004).

Gao X., et al., Tunable focal depth of an apodized focusing optical system, Optical Engineering 44(6), 063001, 1-9, (Jun. 2005).

King, M.C. and D. H. Berry, D.H. A Depth Scanning Microscope, Applied Optics, vol. 10, No. 1, January, pp. 208-210, (1971).

Kerfoot, Christopher A., and Dauffenbach, Lisa M., Quantitative Multiplex Chromagenic Immunohistochemistry, Mosaic Laboratories, www.mosaiclabs.corn, Tuscon Symposium, (2007).

Pieper, R.J. and Korpel A., Image processing for extended depth of field, Applied Optics, vol. 22, No. 10, May 15, pp. 1449-1453, (1983).

Widjanarko, T., et al., A post-processing technique for extending depth of focus in conventional optical microscopy, Optics & Laser Technology 34, pp. 299-305 (2002).

Martini, N. et al., A new high-aperture glycerol immersion objective lens and its application to 3D-fluoresence microscopy, Journal of Microscopy vol. 206 Pt. 2, May 2002, pp. 146-151.

Sanyal, S. and Ghosh, A., High focal depth with a quasi-bifocus birefringent lens, Applied Optics, vol. 39, No. 14, May 10, pp. 2321-2325, (2000).

Darrell, A et al., Accounting for Point Source Propagation Properties in 3D Fluorescence OPT, Proceedings of the 28th IEEE, EMBS Annual International Conference, New York City, USA, Aug. 30-Sep. 3, 2006.

Conchelo, J-A.; Dresser, M.E., Extended depth-of-focus microscopy via constrained deconvolution; Journal of Biomedical Opticas 12 (6), 064026 (Nov./Dec. 2007).

* cited by examiner

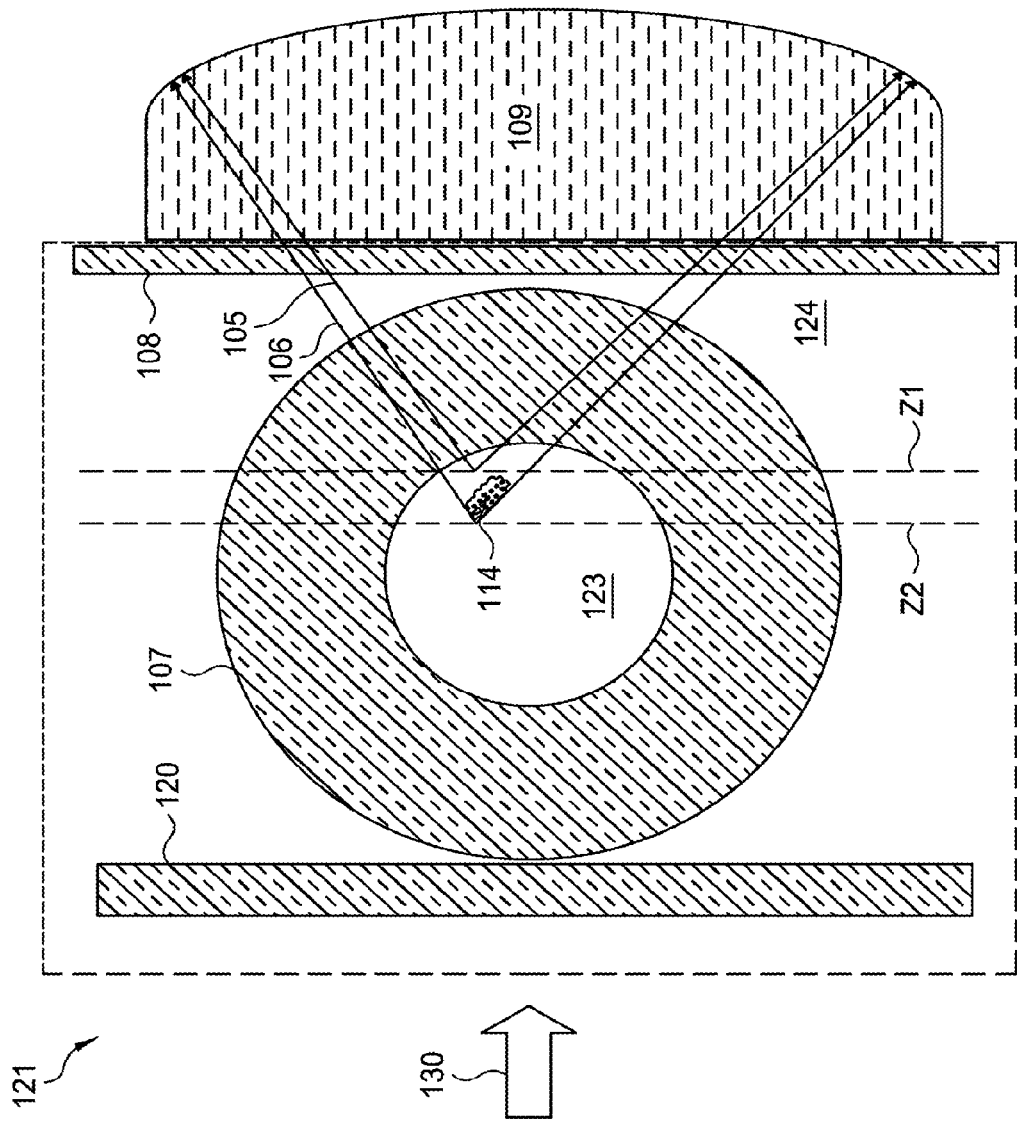

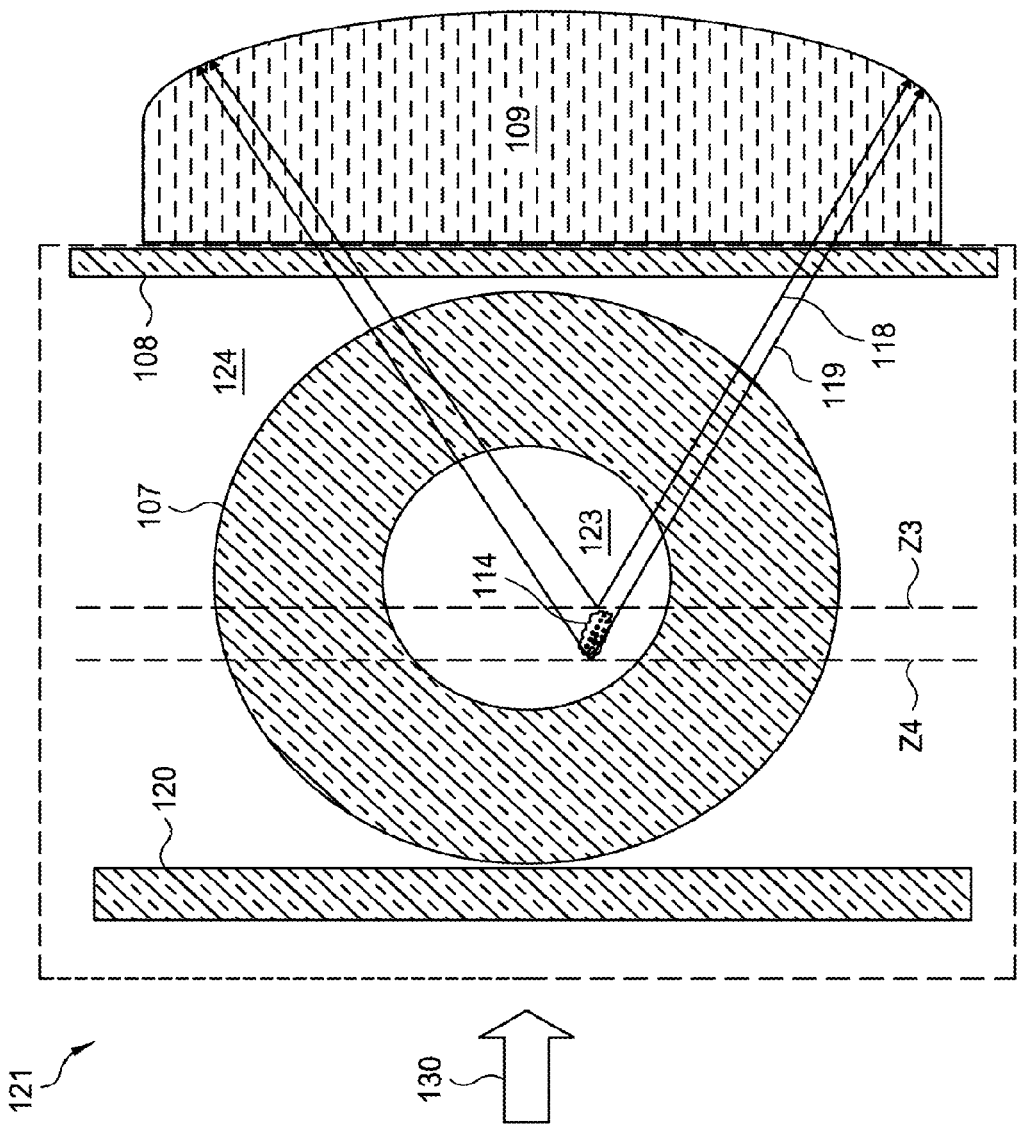

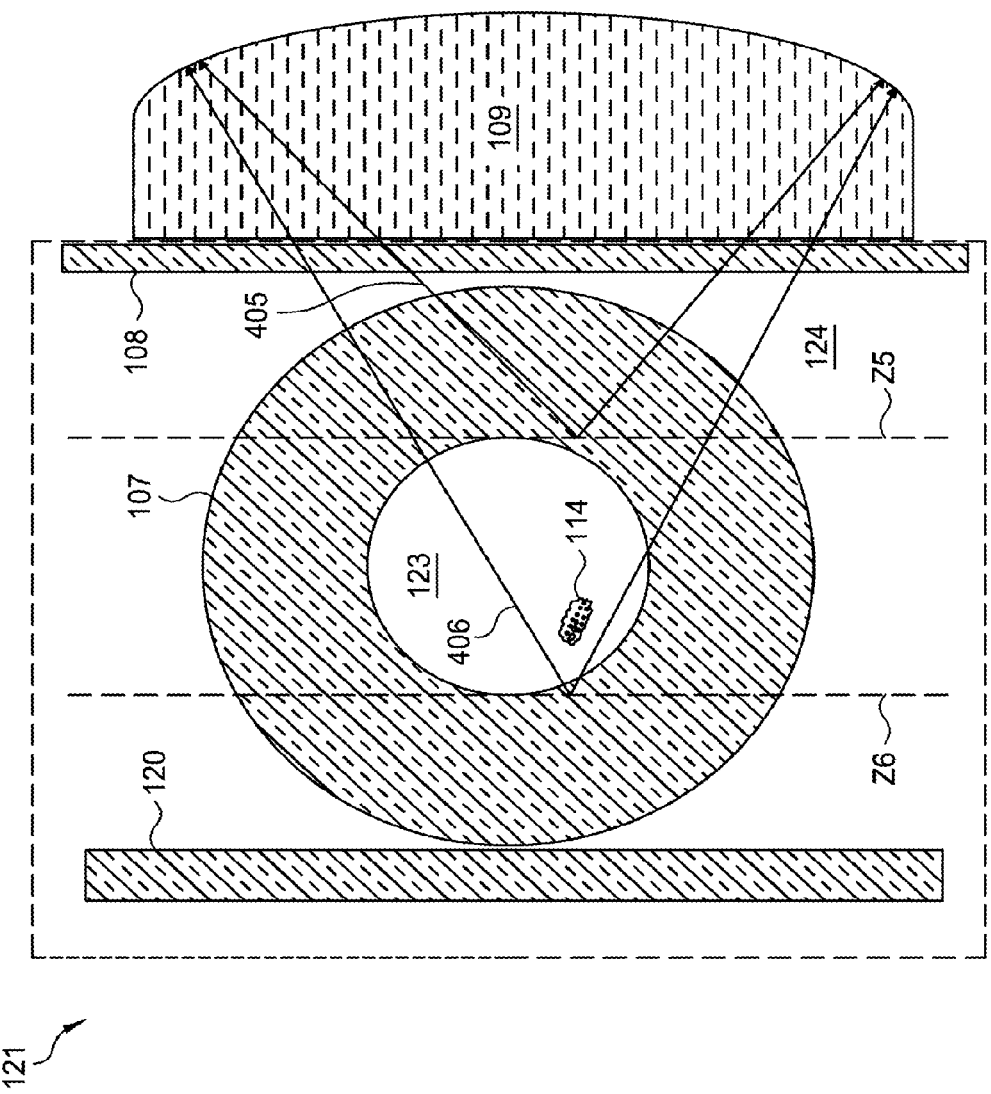

DEPTH OF FIELD EXTENSION FOR OPTICAL TOMOGRAPHY

CROSS-REFERENCE TO RELATED APPLICATIONS

The present invention is a divisional of co-pending U.S. application Ser. No. 11/876,658 to Rahn, et al. entitled "Depth of Field Extension for Optical Tomography," and hereby claims the benefit of the right of priority to the filing date of application Ser. No. 11/876,658. Application Ser. No. 11/876,658 is hereby incorporated by reference.

TECHNICAL FIELD

The present invention relates to optical tomographic imaging systems in general, and, more particularly, to optical projection tomography, in which a small object, such as a biological cell, is positioned in a capillary tube for imaging by a microscope.

BACKGROUND

Advances in imaging biological cells using optical tomography have been developed by Nelson as disclosed, for example, in U.S. Pat. No. 6,522,775, issued Feb. 18, 2003, and entitled "Apparatus and method for imaging small objects in a flow stream using optical tomography," the full disclosure of which is incorporated by reference. Further developments in the field are taught in Fauver et al., U.S. patent application Ser. No. 10/716,744, filed Nov. 18, 2003 and published as US Publication No. US-2004-0076319-A1 on Apr. 22, 2004, entitled "Method and apparatus of shadowgram formation for optical tomography," (Fauver '744) and Fauver et al., U.S. patent application Ser. No. 11/532,648, filed Sep. 18, 2006, entitled "Focal plane tracking for optical microtomography," (Fauver '648) the full disclosures of which are also incorporated by reference.

Processing in such an optical tomography system begins with specimen preparation. Typically, specimens taken from a patient are received from a hospital or clinic and processed to remove non-diagnostic elements, fixed and then stained. Stained specimens are then mixed with an optical gel, inserted into a micro-capillary tube and images of objects, such as cells, in the specimen are produced using an optical tomography system. The resultant images comprise a set of extended depth of field images from differing perspectives called "pseudo-projection images." The set of pseudo-projection images can be reconstructed using backprojection and filtering techniques to yield a 3D reconstruction of a cell of interest.

The 3D reconstruction then remains available for analysis in order to enable the quantification and the determination of the location of structures, molecules or molecular probes of interest. An object such as a biological cell may be labeled with at least one stain or tagged molecular probe, and the measured amount and location of this probe may yield important information about the disease state of the cell, including, but not limited to, various cancers such as lung, breast, prostate, cervical and ovarian cancers.

In Optical Projection Tomography Microscopy (OPTM) systems as described, for example, in Fauver '648, about 250 sample images taken over a 180-degree rotation are required to adequately sample the volume of a cell nucleus randomly distributed in a flow stream within a 50 micron capillary tube.

The present disclosure provides new and novel techniques for providing higher resolution and improved signal to noise ratio in order to reduce sampling requirements while maintaining acceptable resolution.

In one type of optical tomography system, as described in Fauver '744 and constructed by VisionGate, Inc., the depth of field of the imaging optics is extended by scanning an objective lens transverse to a capillary tube containing a specimen. A piezoelectric transducer (PZT) actuator transversely moves the objective lens sinusoidally several times per second in order to scan a series of focal planes though a specimen. By using a PZT actuator to move the objective lens, a focal plane moving through the specimen has its speed limited by inertia inherent in moving the objective lens mass rapidly along the optical axis through the specimen. Typically, an upper limit of the scan rate is roughly 60 cycles per second. With well-synchronized rotation and objective scanning, an image can be acquired on the down-stroke as well as the up-stroke of the PZT actuator, allowing up to 120 images per second to be acquired. While this is a useful acquisition rate, it can be significantly improved through the apparatus, systems and methods disclosed herein.

BRIEF SUMMARY OF THE DISCLOSURE

An optical tomography system for viewing an object of interest includes a microcapillary tube viewing area for positioning the object of interest in an optical path including a detector. A motor is located to attach to and rotate a microcapillary tube. A device is arranged for transmitting broadband light having wavelengths between 550 nm and 620 nm into the microcapillary tube viewing area. A hyperchromatic lens is located to receive light transmitted through the microcapillary tube viewing area. A tube lens is located to focus light rays transmitted through the hyperchromatic lens, such that light rays from multiple object planes in the microcapillary tube viewing area simultaneously focus on the at least one detector.

BRIEF DESCRIPTION OF THE DRAWINGS

FIG. 4A schematically shows a detail of the object space at one viewing angle in an optical tomography system incorporating a hyperchromatic optical lens.

FIG. 4C schematically shows a detail of the object space at a second viewing angle in an optical tomography system incorporating a hyperchromatic optical lens.

FIG. 7C schematically illustrates the object space for a second viewing angle for a hyperchromatic optical tomography system incorporating a long depth of field.

Figure 1:
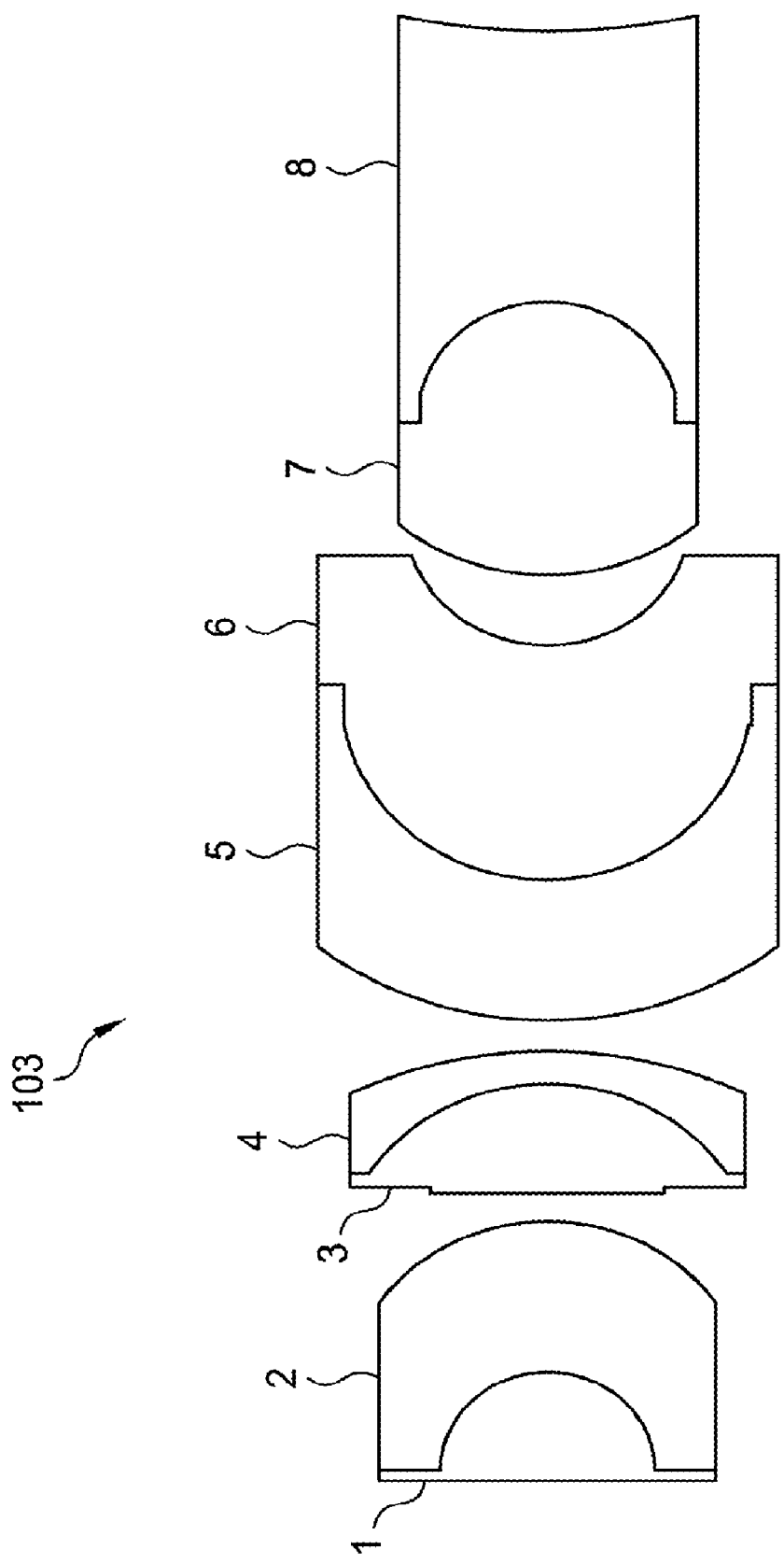
FIG. 1 schematically shows an example of a design for a hyperchromatic optical lens system.
Figure 2B:
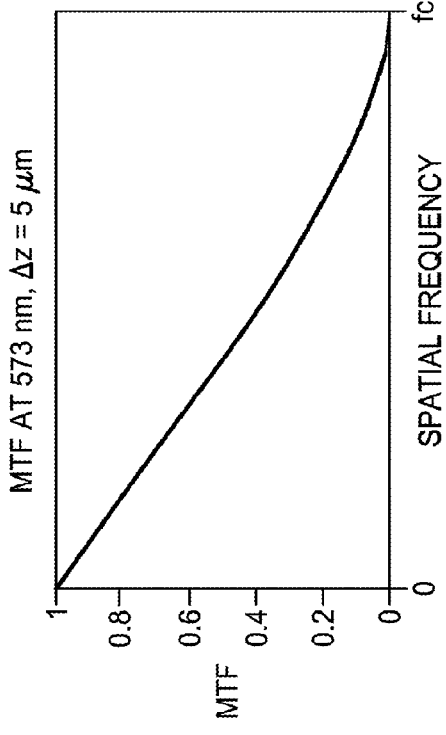
FIG. 2A-FIG. 2D schematically show qualitative examples of simulated monochromatic modulation transfer functions (MTFs) for each of four wavelengths, as they might be evaluated at four separate image planes.
Figure 2D:
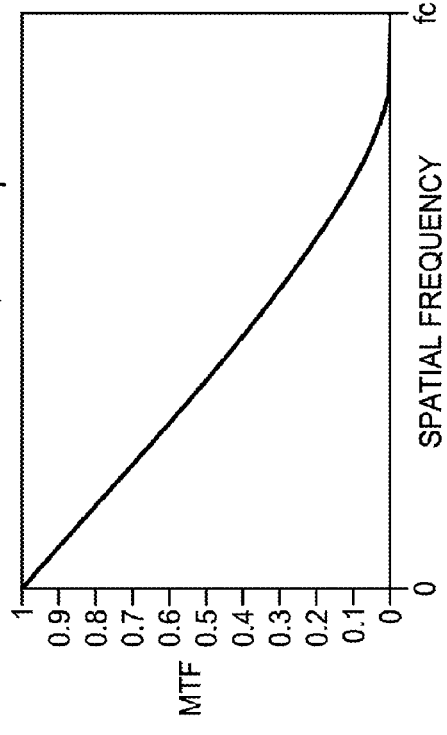
Figure 2A:
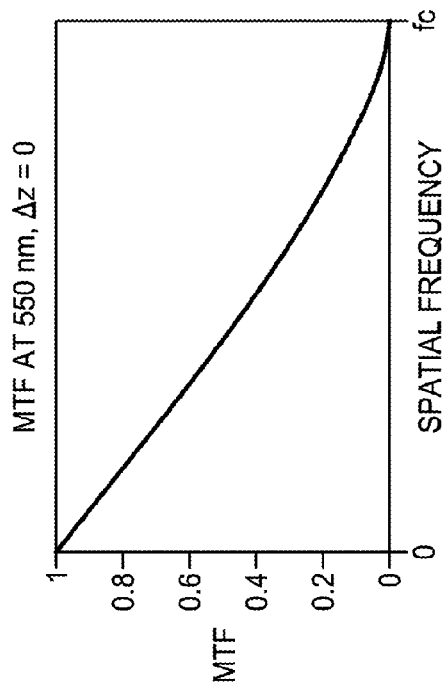
Figure 2C:
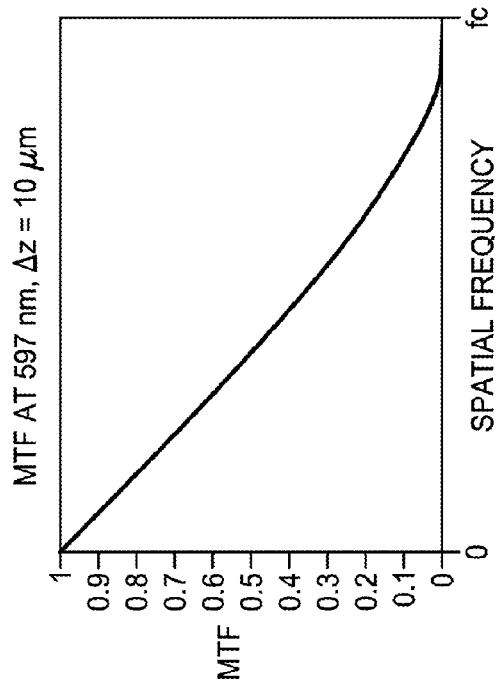
Figure 3A:
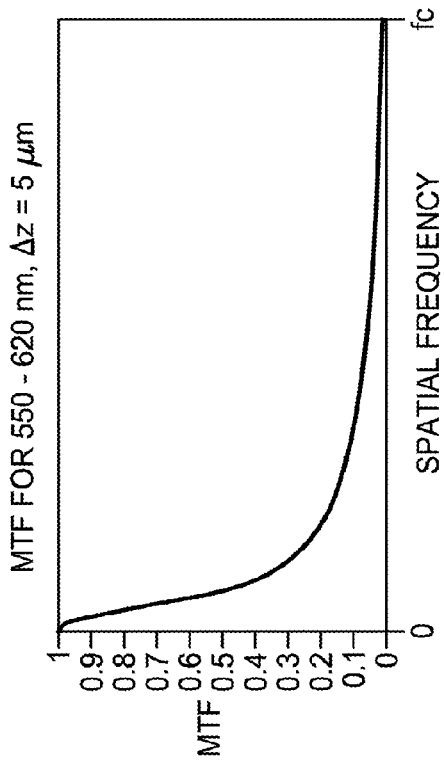
FIG. 3A-FIG. 3D schematically show qualitative examples of simulated polychromatic modulation transfer functions over a range of wavelengths, as they might be evaluated at four separate image planes.
Figure 3B:
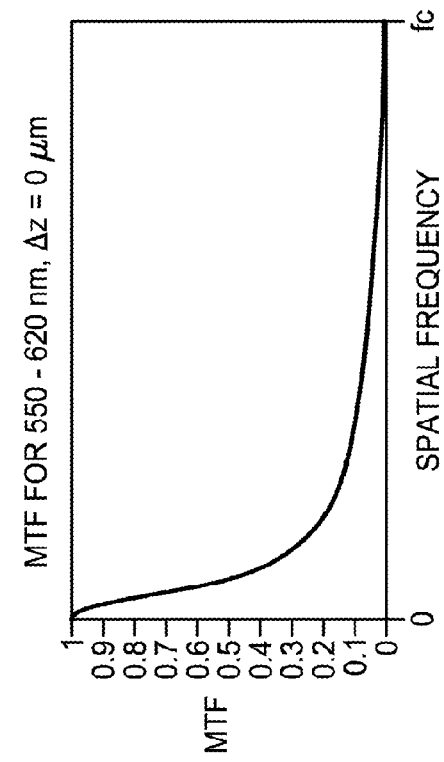
Figure 3C:
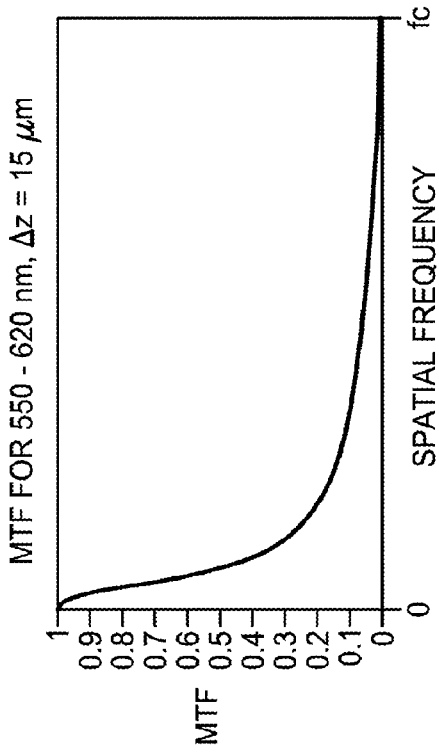
Figure 3D:
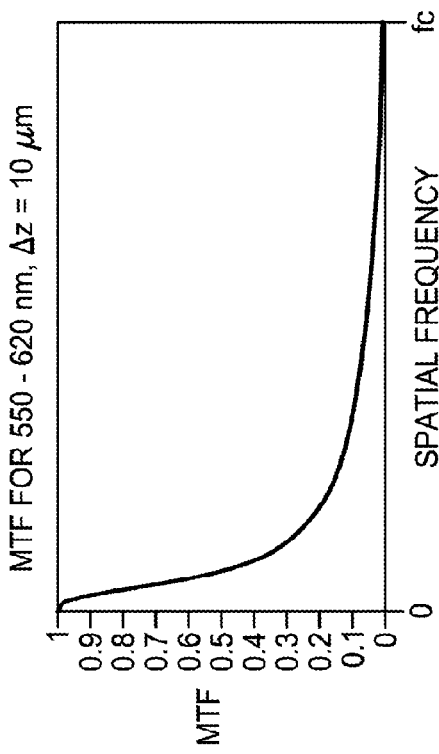

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments and systems for imaging an object of interest. Several features of methods and systems in accordance with example embodiments of the invention are set forth and described in the Figures. It will be appreciated that methods and systems in accordance with other example embodiments of the invention can include additional procedures or features different than those shown in Figures. Example embodiments are described herein with respect to biological cells. However, it will be understood that these examples are for the purpose of illustrating the principals of the invention, and that the invention is not so limited.

Additionally, methods and systems in accordance with several example embodiments of the invention may not include all of the features shown in these Figures. Throughout the Figures, like reference numbers refer to similar or identical components or procedures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or various combinations of these terms means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally as used herein the following terms have the following meanings when used within the context of optical microscopy processes:

"Capillary tube" has its generally accepted meaning and is intended to include transparent microcapillary tubes and equivalent items with an inside diameter of 100 microns or less.

"Depth of field" is the length along the optical axis within which the focal plane may be shifted before an unacceptable image blur is produced.

"Object" means an individual cell or other entity.

"Pseudo-projection" includes a single image representing a sampled volume of extent larger than the native depth of field of the optics.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"Sample" means a finished cellular preparation that is ready for analysis, including all or part of an aliquot or specimen.

Chromatic Aberration Depth of Field Extension

Most simple lenses will produce wavelength-dependent focal positions known as chromatic focal shift. Chromatic aberrations are typically undesirable in a lens. However, for a sufficiently broad absorption spectrum in a biological sample, the dispersion of chromatic aberration can in effect extend the depth of field image of an absorptive object or feature.

Wavelength-dependent lens material will produce a lens with chromatic aberrations. Nearly all lens materials can have both positive and negative index shifts with wavelength. Lens designers typically choose lens materials to compensate for the chromatic focal plane shifts, resulting in a net chromatic focal shift near zero. For an example of an immersion microscope objective which is corrected for spherical and axial chromatic aberrations see U.S. Pat. No. 5,517,360 issued May 14, 1996 to T Suzuki, entitled "Immersion microscope objective."

Changing the design parameters to emphasize, rather than minimize, the chromatic focal shift can create large chromatic, or hyperchromatic, aberrations in the optical path. Such hyperchromatic aberrations can simultaneously focus multiple focal depths on a detector, with each optical wavelength forming an image at the detector of a separate focal plane within the object. This widens the range of focal positions over a limited desired wavelength range. For a specimen with a narrow absorption peak in the stain or contrast agent, a lens can be designed to include optical field extension elements to extend the dispersion over many microns to form an extended depth of field optical system for a narrow range of wavelengths. The optical components and materials are chosen to optimize chromatic dispersion within the stain absorption range.

When employing chromatic aberration, it may be advantageous to alter the relative makeup of the spectral components to compensate for factors that may affect the composition of the image. These may include, but are not limited to, wavelength dependencies of the contrast agent or stain, the camera response, and transmission through the optical materials. The spectral composition may be altered by, for example, incorporating in the illumination, collection, and/or imaging optics a filter that attenuates some wavelengths more than others.

As an example, a limited extension of the depth of field can be achieved for a narrow range of wavelengths accommodating existing stain absorption curves, such as the hematoxylin family of stains. Stains in the hematoxylin family exhibit a peak absorption in the wavelength range from 550 to 620 nanometers.

Example 1

One example of a hyperchromatic objective lens 103, suitable for use in a hyperchromatic system, is depicted in FIG. 1. This compound lens comprises eight optical elements 1-8 of which optical elements 1 and are cemented together to form a first doublet, and optical elements 3 and 4 are cemented together to form a second doublet, 5 and 6 are cemented together to form a third doublet, and 7 and 8 are cemented together to form a fourth doublet. The first surface of 1 is flat or slightly convex, so as to avoid trapping air in a cavity when this surface comes in contact with an immersion liquid such as oil or water. An example prescription for the objective 103 follows.

| Element | Material (Schott designation) | Front Radius of Curvature (mm) | Back Radius of Curvature (mm) | Center Thickness (mm) |
|---|---|---|---|---|
| 1 | SF57 | 200 | −3.17 | 3.54 |
|   | LAK14 | 3.17 | −5.92 | 5.08 |
|   | Air | — | — | 1 |
| 3 | KZFSN4 | 104.5 | −6.55 | 3.64 |
| 4 | SF6 | 6.55 | −13.77 | 1 |
|   | Air | — | — | 1 |
| 5 | SF64 | 10.73 | 6.27 | 4.75 |
| 6 | LASF40 | −6.27 | 4.47 | 7.88 |
|   | Air | — | — | 2.24 |
| 7 | SK2 | 7.23 | −3.95 | 9.05 |
| 8 | F2 | 3.95 | 19.37 | 8.83 |

The location of the aperture stop may be chosen to provide telecentricity, and to minimize lateral color (also known as chromatic difference of magnification). Component materials are commercially available from, for example, Schott North America, Inc. Elmsford, N.Y. 10523.

As shown in the examples described hereinbelow with reference to the figures, lens system 103, when placed in front of a tube lens having a focal length of 180 mm, will provide 60× magnification at numerical aperture (NA) equal to 0.9 over a wavelength range from 550 nm to 620 nm, provided that the space between the front surface of the first element 1 and the top of a cover slip positioned in the field of view of the lens is filled with water. The cover slip is typically about 130 microns thick, while the water-filled space between the cover slip and the lens may be about 200 microns thick. An object is focused on the imaging plane of the camera over a range of 15 microns at separate wavelengths over a 200-micron diameter field of view. In this example embodiment, the portion of the object in a first plane is focused by the 550-nm portion of the incident light, a second plane located 5 microns below the first plane is focused by the 573-nm portion of the incident light, a third plane located 10 microns below the first plane is focused by the 597-nm portion of the incident light, and a fourth plane located 15 microns below the first plane is focused by the 620-nm portion of the incident light.

System MTFs

Referring now to FIG. 2A through FIG. 2D qualitative examples of simulated monochromatic modulation transfer functions (MTFs) for each of four wavelengths, as evaluated at four separate image planes. Throughout FIG. 2A-FIG. 3D the vertical axis represents system MTF and the horizontal axis represents frequency ranging from 0 to a cutoff frequency, fc, where fc is the highest frequency with a non-zero MTF. An MTF similar to the one shown in FIG. 2A could, in principle, be measured by placing a 2D optical test target in the object space, illuminating it with narrowband light having a wavelength of about 550 nm, and finding the best focus. Changing the wavelength to about 573 nm and moving the focal position by 5 microns may produce the MTF shown in FIG. 2B. Repeating this process for about 597 nm and again for about 620 nm yields the MTFs shown in FIG. 2C and FIG. 2D, respectively. The in-focus information from the entire volume of an object may be acquired simultaneously, for an object thickness up to 15 microns.

Referring now to FIG. 3A through FIG. 3D qualitative examples of simulated polychromatic modulation transfer functions (MTFs) are shown for an optical projection system where the illumination consists of a band of wavelengths between about 550 nm and 620 nm are shown. An MTF similar to the one shown in FIG. 3A could, in principle, be measured by placing a 2D optical test target in the object space, illuminating it with broadband light having a band of wavelengths in the range of about 550-620 nm, and finding the best focus, $\Delta Z=0$. Moving the focal position by 5 microns to focus $\Delta Z=5$ microns qualitatively yields the MTF shown in FIG. 3B. Moving the focal position by 10 microns, $\Delta Z=10$ microns, and by 15 microns, $\Delta Z=15$ microns, qualitatively yields the MTFs shown in FIG. 3C and FIG. 3D respectively. It is to be understood that other prescriptions and optical designs may be employed without departing from the spirit of this embodiment.

The hyperchromatic optical system may advantageously be incorporated into an OPTM system. A translation device, such as, for example, a piezoelectric transducer (PZT) may be used to apply a single, low-speed translation of the objective lens over the course of a 360-degree set of scans. The lens translation keeps the object of interest within a focus interval of about 15 microns, even while the tube rotation causes the object to translate along the optical axis by as much as the internal diameter of the rotating capillary during the 360-degree scan. In contrast to earlier embodiments, a high-speed scan taken at each perspective is no longer required. As a result, image acquisition speed is no longer limited by the speed of the PZT translation device. In addition, synchronization between the tube rotation and translation motion of the lens no longer needs to be as precise, thereby reducing the complexity of the OPTM instrument control system.

Now referring to FIG. 4A a detail of object space at one viewing angle in an optical tomography system incorporating a hyperchromatic optical lens is schematically shown. A cell 114 lies between a first object plane Z1 and a second object plane Z2 inside a microcapillary tube 107. The tube 107 may have, for example, an inner diameter of 50 microns, and the separation between the first object plane and the second object plane may be, for example, 15 microns. The microcapillary tube 107 is preferably filled with an optical matching medium 123 matching the internal index to the tube's index of refraction.

Figure 4B:
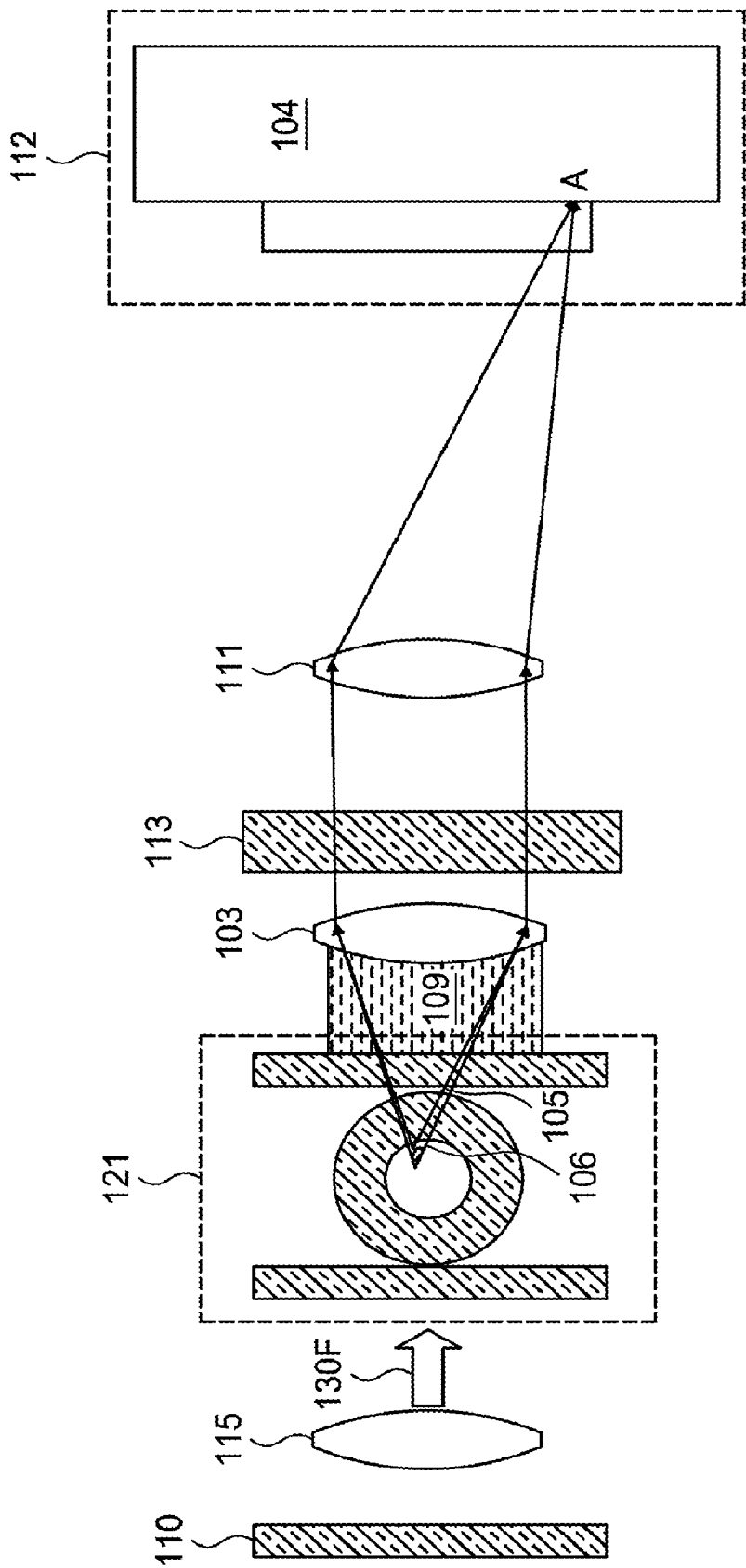
FIG. 4B schematically shows the operation of the optical tomography system depicted schematically in FIG. 4A.

In one example embodiment, an assembly 121 preferably includes the microcapillary tube 107 placed in a viewing area between a first flat optical surface 120, which may comprise a standard microscope slide, and a second flat optical surface 108, which may comprise a standard microscope coverslip. The interstices between the tube 107 and the flat surfaces 108, 120 are filled with optical oil 124, or an equivalent, having an index of refraction that also substantially matches those of the tube 107, the flat surfaces 108, 120, and the optical gel 123. The assembly 121 can be mounted on a microscope, and an optical immersion fluid 109, comprising, for example, oil, water, or air, is placed on the side of the assembly 121 that faces hyperchromatic optics (as shown in FIG. 4B). The outer diameter of the tube 107 may be, for example about 250 microns, the thickness of the coverslip 108 may be about 170 microns, and the thickness of the immersion fluid 109 may be between about 100 and 300 microns.

Broadband light 130 having wavelengths between a first wavelength λ1 (e.g., λ1=about 550 nm) and a second wavelength λ2 (e.g., λ2=about 620 nm) is transmitted into the tube 107 by means of, for example, a condenser lens system. A first set of ray paths 105 of light having wavelength λ1 travel from the first object plane Z1 and into the immersion fluid 109. A second set of ray paths 106 of light having wavelength λ2 travel from the second object plane Z2 and into the immersion fluid 109. Although not depicted in FIG. 4A, it may be understood that light having wavelengths λn, where λn is a wavelength between λ1 and λ2, travel from intermediate object planes, Zn, located between the first object plane and the second object plane, along ray paths similar to 105 and 106.

With reference to FIG. 4B, the operation of this system may be more fully understood. A chromatic filter 110 and a condenser lens 115 provide illumination 130F having the desired upper and lower wavelength limits (λ1, λ2). The incident light passes through the tube assembly 121, containing, for example, a biological cell 114. The ray paths 105 and 106,106, having wavelengths λ1 and λ2 and beginning near the cell 114 at object planes Z1 and Z2, respectively, pass through the immersion fluid 109 and the hyperchromatic objective lens system 103, and are substantially collimated when they reach the tube lens 111. They then pass through the tube lens 111 which may, for example, have a focal length of about 180 mm, and achieve focus A on the image plane 104 of a CCD camera 112. The objective lens 103 is mounted on a PZT 113, which is capable of moving the objective 103 further from the tube lens 111 and closer to the object planes Z1 and Z2.

Light having a wavelength λn, where the λn wavelength is a wavelength having a value between λ1 and λ2, will travel from intermediate object planes, Zn, located between plane Z1 and plane Z2, along ray paths similar to 105 and 106, and also come to a focus on image plane 104. The wavelength of λn, relative to λ1 and λ2, determines where the intermediate object plane is located, relative to object planes Z1 and Z2, in order for it to be focused on image plane 104.

Figure 4D:
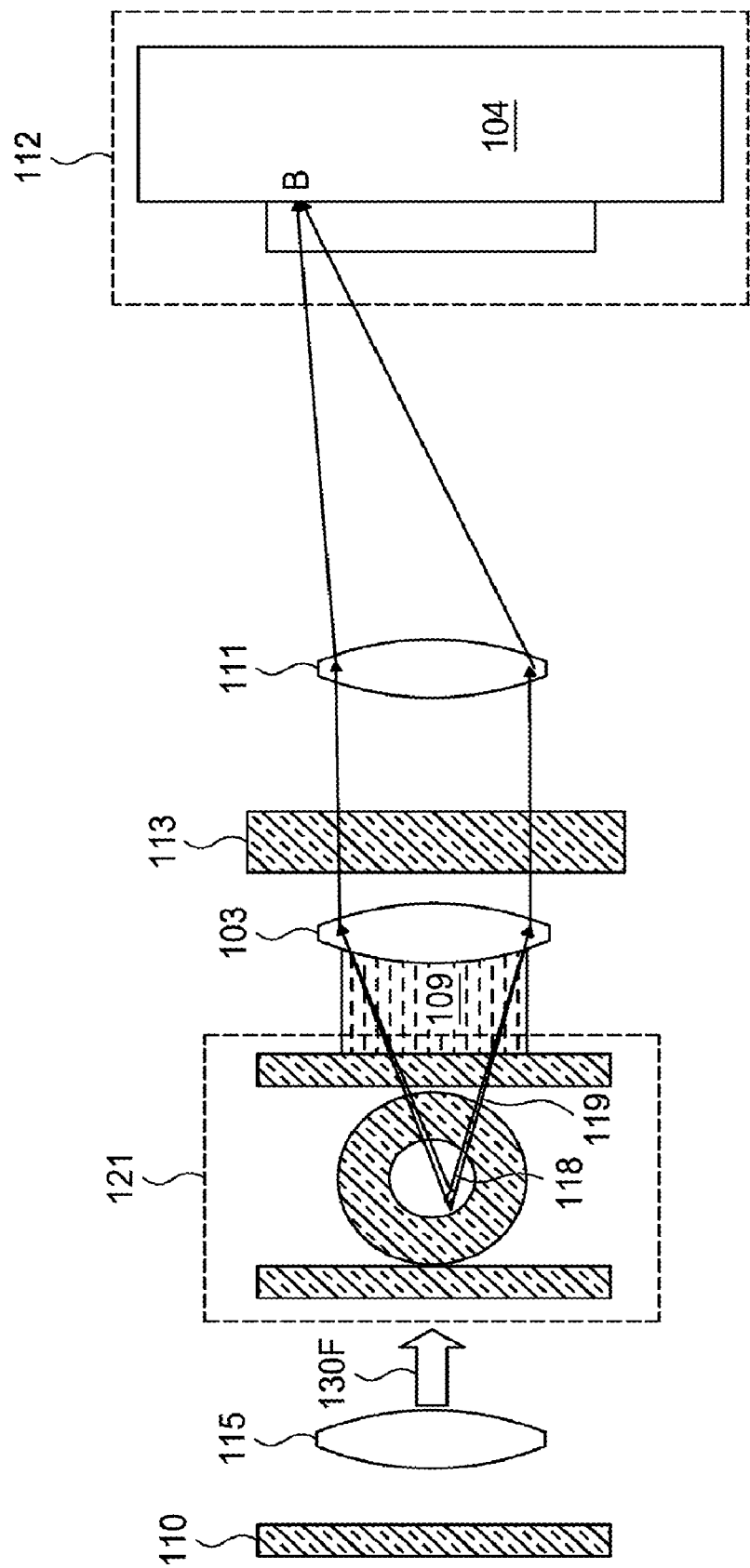
FIG. 4D schematically shows the operation of the optical tomography system depicted schematically in FIG. 4C.

Now referring to FIG. 4C, the system of FIG. 4A is shown after the microcapillary tube 107 has rotated, causing the cell 114 to change its location and orientation as well. To compensate for this motion, the PZT 113 (as shown, for example in FIG. 4B) moves the objective lens 103 by an amount sufficient to cause the focused light on the image plane 104 to originate from the a second set of object planes Z3 and Z4, via ray path 118 from object plane Z3 for light of wavelength λ1, and via ray path 119 from object plane Z4 for light of wavelength λ2. Those skilled in the art and having the benefit of this disclosure will understand that light having varying wavelengths λn between λ1 and λ2 will travel from intermediate object planes, Zn, located between object planes Z3 and Z4 along ray paths between ray paths 118 and 119 will also come to a focus on image plane 104. The wavelengths λn, relative to λ1 and λ2, determines where object planes Zn must be located, relative to Z3 and Z4, in order for it to be focused on image plane 104. FIG. 4D shows the system detailed in FIG. 4C, in particular, illustrating that the PZT 113 has moved the objective 103 so that the focused image is shifted to focus B on image plane 104.

Those skilled in the art and having the benefit of this disclosure will appreciate that the system depicted in FIG. 4A-FIG. 4D allows the camera 112 to acquire an image similar to the defined pseudo-projection produced by scanning a well-corrected objective lens over the entire thickness of the cell 114 and further permits the acquisition of multiple pseudo-projections from multiple angles, without the necessity of moving the objective lens 103 at a high speed via high-frequency drive of the PZT scanning mechanism 113.

Another embodiment employs the hyperchromatic optical path described previously, having an aberration that produces focus over the thickness of the object (e.g., 15 microns) for wavelengths within the range of constant absorption by the stain. This embodiment further includes a Chromatic Filter Array (CFA) in the optical path, preferably located just before the image plane 104. The CFA may consist of two or more types of pixels, each pixel having a size corresponding to the pixel size of the camera 112 imaging surface 104. Each type of pixel passes a separate range of wavelengths. An example of a CFA, having much wider bandpass ranges than the one described as part of this invention, is the Bayer filter, as described in U.S. Pat. No. 4,081,277, "Method for making a solid-state color imaging device having an integral color filter and the device" issued on Mar. 28, 1978 to Brault, et al.

Figure 5:
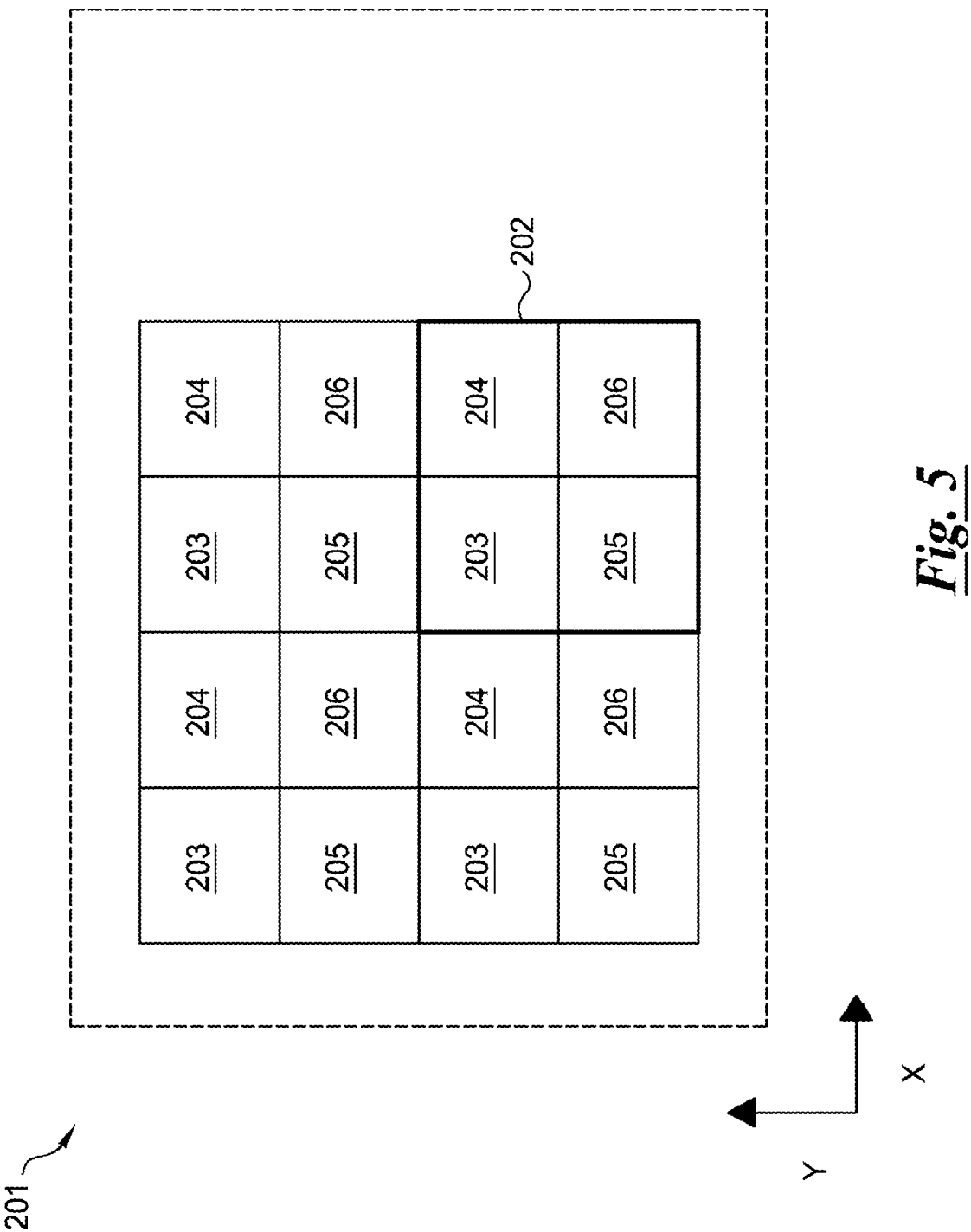
FIG. 5 schematically shows an example of a design for a chromatic filter array.

Referring now to FIG. 5, an example of a design for a chromatic filter array is schematically shown. CFA 201 includes a plurality of pixel types in a unit cell 202. In one example, the plurality of pixel types includes four pixel types 203, 204, 205, 206 included in the unit cell 202. The four pixel types pass only wavelengths, of 550-567 nm, 567-584 nm, 584-601 nm, and 601-618 nm, respectively. The CFA 201 must comprise a sufficient number of unit cells 202 to cover a substantial portion of the image surface 104. For example, if the image plane 104 comprises 900×1600 pixels, then the CFA 201 may advantageously comprise 450×800 unit cells 202, each unit cell 202 in turn comprising a 2×2 matrix of one each of filter pixel types 203, 204, 205, and 206. This design may limit the spatial resolution by a factor of two, due to the use of only one-fourth of the pixels for each wavelength. However, this is in practice not an issue, as long as the pixel-limited resolvable size (equivalent, with the CFA included, to 4*[pixel size]/magnification) is less than the desired optical resolution (in this example, 500 nm). Under typical conditions of camera pixel size=7.4 microns and magnification=60, this requirement is fulfilled. The light intensity reaching each CCD pixel in this embodiment is reduced by a factor of four due to the four-wavelength CFA. This reduction is also not a problem in practice, as the source intensity can be increased to provide higher light levels without requiring longer camera exposure times.

Figure 6A:
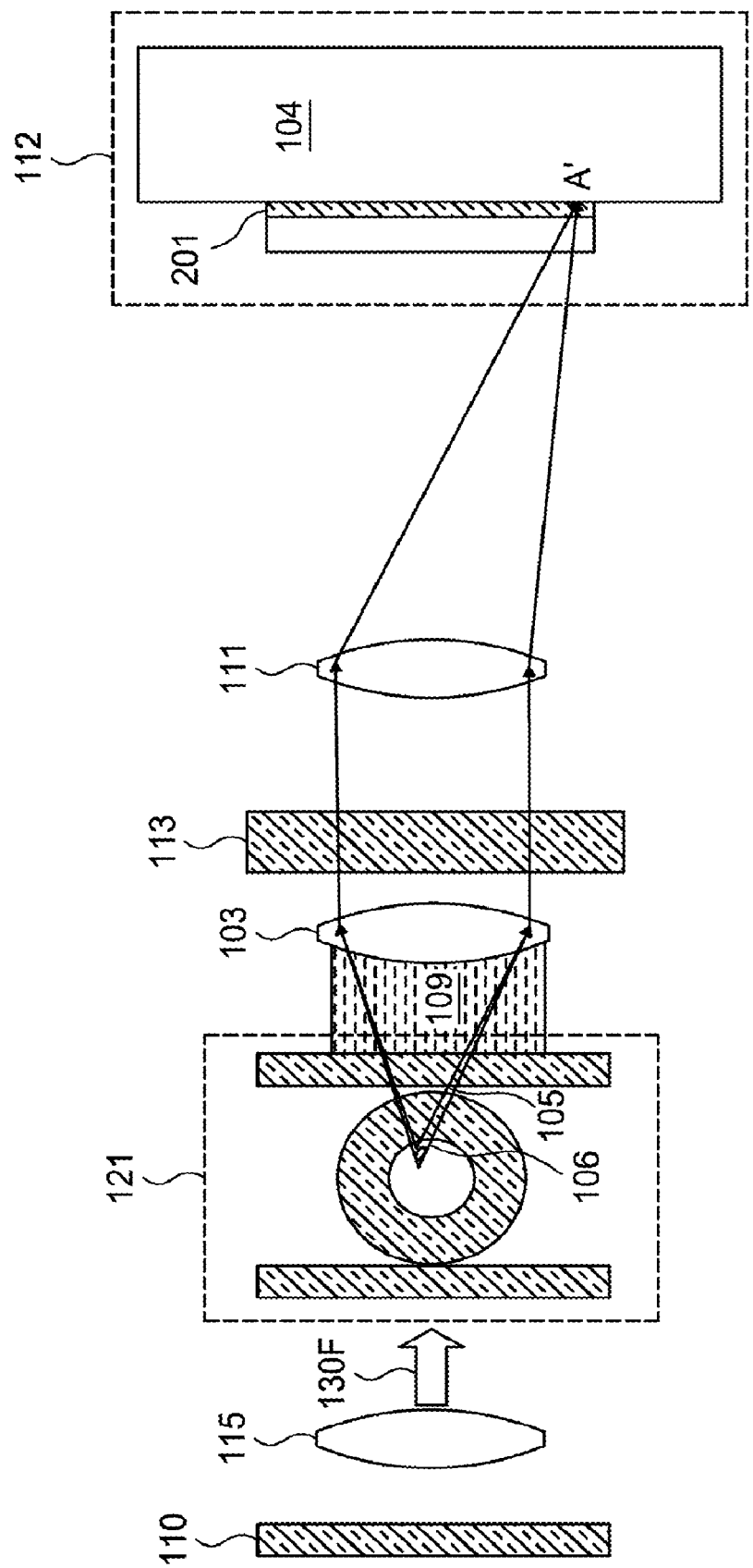
FIG. 6A schematically illustrates a first viewing angle for a hyperchromatic optical tomography system incorporating a chromatic filter array.
Figure 6B:
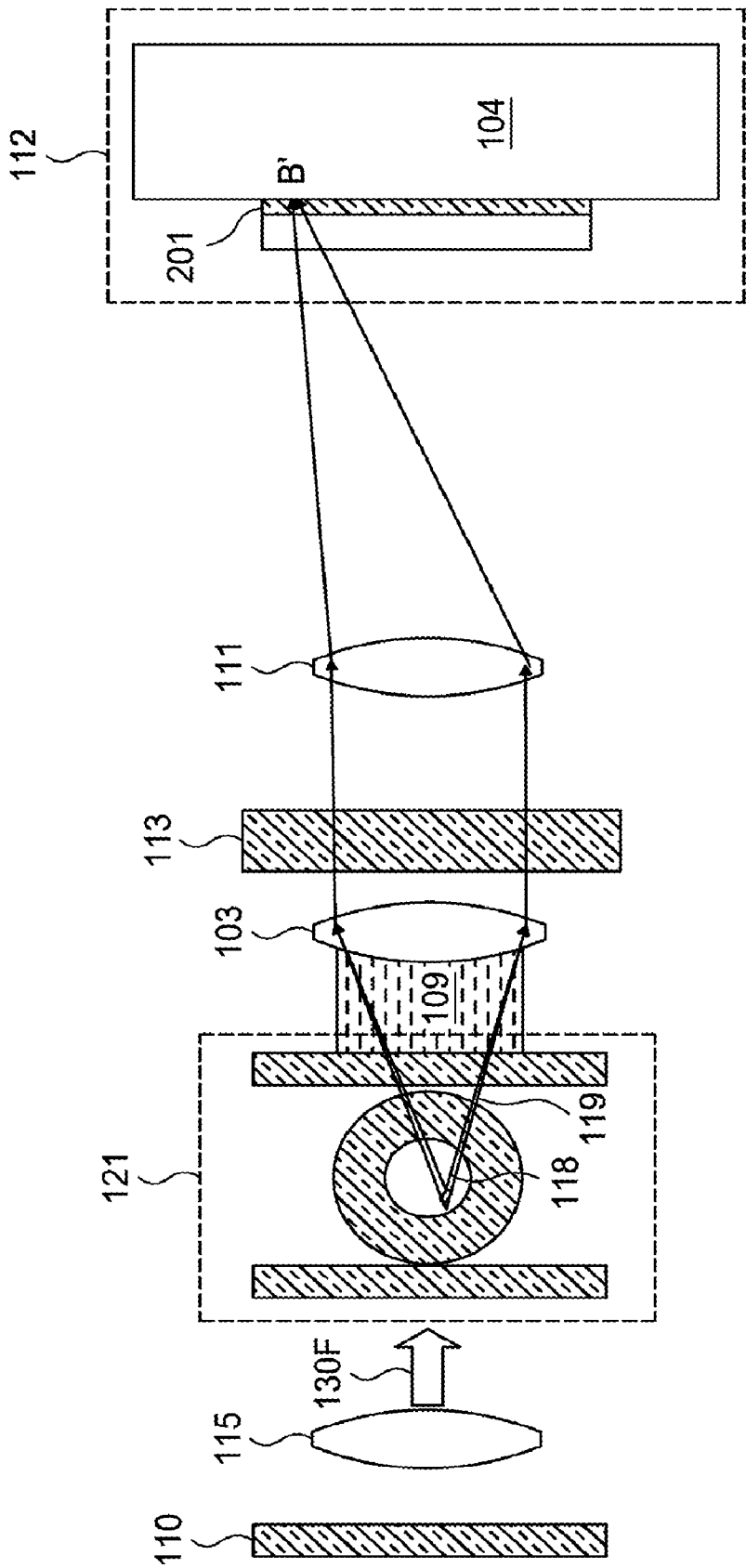
FIG. 6B schematically illustrates a first viewing angle for a hyperchromatic optical tomography system incorporating a chromatic filter array.

With reference jointly to FIG. 6A and FIG. 6B, another example of the operation of a hyperchromatic system incorporating a CFA 201 is illustrated. The system is similar to the one depicted in FIGS. 4A and 4C, with the addition of the CFA 201 on the image surface 104 of the camera 201. Due to translation of the objective 103 along the optical axis of the system, the focus point shifts from focus point A' in FIG. 6A to focus point B' in FIG. 6B.

The inclusion of the CFA 201 makes it possible to separate the signals from two or more (in this example, four) focal ranges, thereby decreasing the amount of defocusing that contaminates the in-focus signal. By saving each focal range separately, they may be combined digitally during post-acquisition processing, permitting an increase in the dynamic range of the combined images, and consequently improving the spatial resolution and contrast of the combined images. Alternatively, the images that result from each wavelength can be processed as two or more separate sets of data, and not combined until after each has been separately tomographically reconstructed, thus providing an improvement in spatial resolution and contrast.

Figure 7A:
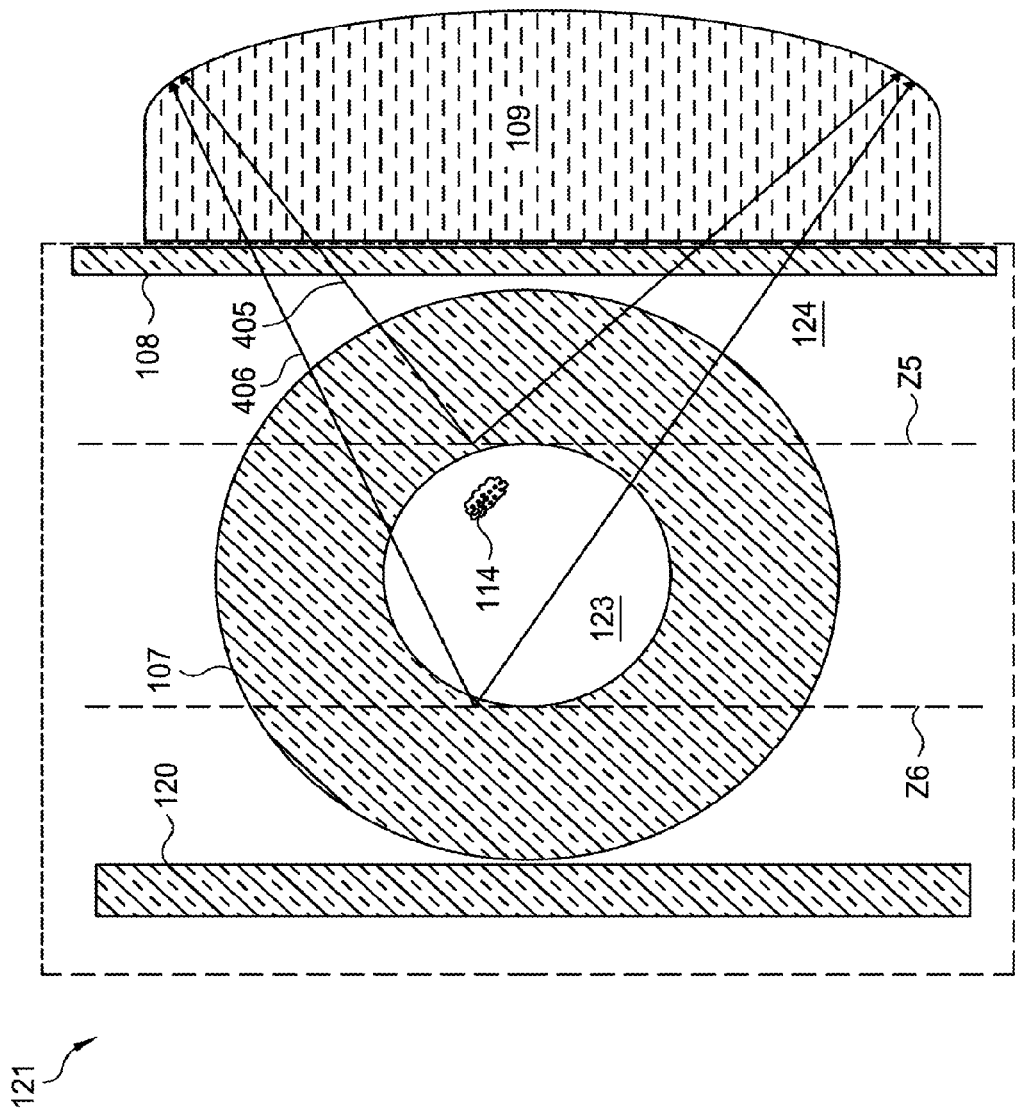
FIG. 7A schematically illustrates object space for a first viewing angle for a hyperchromatic optical tomography system incorporating a long depth of field.
Figure 7B:
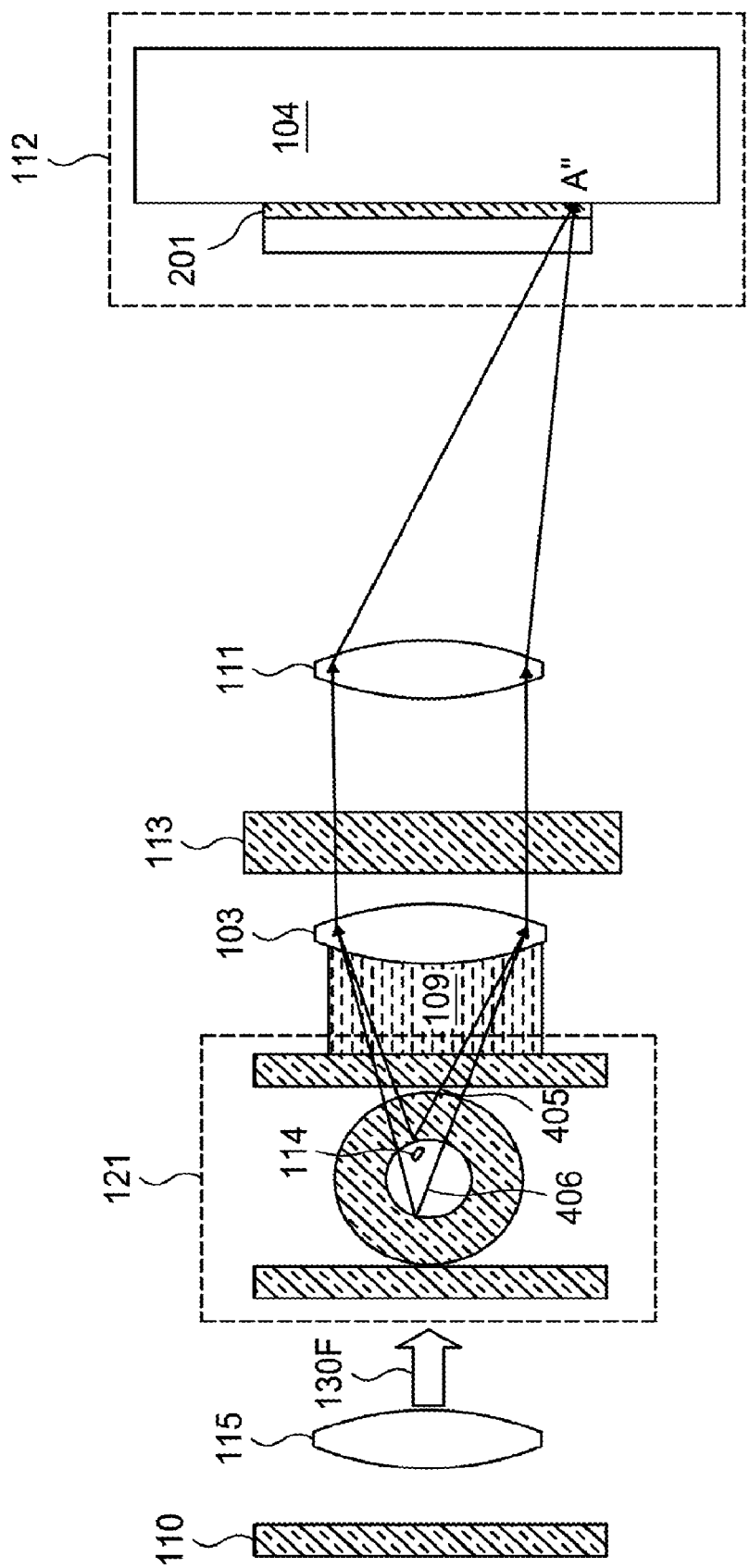
FIG. 7B schematically illustrates a first viewing angle for a hyperchromatic optical tomography system incorporating a long depth of field.

Referring now jointly to FIG. 7A and FIG. 7B, object space for a first viewing angle, $\theta_1$, for a hyperchromatic optical tomography system incorporating a long depth of field is schematically illustrated. The extended limits of the focal range, combined with the CFA 201, make a lens transducer, such as PZT 113, unnecessary for the operation of the system. Another pair of object planes Z5 and Z6 corresponds to wavelengths $\lambda 1$ and $\lambda 2$, respectively. The object planes are located at the extrema of the inner diameter of the microcapillary tube 107. Because object planes Z5 and Z6 are located at the extrema of the inner diameter of the microcapillary tube 107, the location of object planes Z5 and Z6 remain constant relative to the objective lens even as the tube 107 rotates, causing the cell 114 to change its location relatively to the objective lens. For a microcapillary tube 107 having an inner diameter of 50 microns, the separation between object planes Z5 and Z6 should, preferably, be at least 50 microns. The ray paths 405 and 406, comprising light of wavelengths $\lambda 1$ and $\lambda 2$, respectively, travel through object planes Z5 and Z6, respectively, and reach the CFA 201, where $\lambda 1$ is transmitted only through, for example, CFA pixels of the first type 203, and $\lambda 2$ is transmitted only through, for example, CFA pixels of the last type 206.

Owing to the existence of the multiple pixel types in the unit cell of the CFA, each pixel type only collects light from a portion of the interval between the object planes Z5 and Z6. For the four-color CFA 201 shown in FIG. 5 as described above, each interval is, preferably, non-overlapping, and therefore only one-fourth of the total interval is transmitted through any pixel type and collected by the camera 112.

As an example, if the focal plane separation is 50 microns, and the wavelength range is 550 to 618 nm, then camera pixels lying directly behind pixel type 203 will detect only light having wavelengths between 550 and 567 nm, corresponding to object planes between object plane Z5 and Z5+12.5. In a similar manner, camera pixels lying directly behind pixel type 204 will detect only light having wavelengths between 567 and 584 nm, corresponding to focal planes between object planes located between Z5+12.5 microns and Z5+25 microns. Camera pixels lying directly behind pixel type 205 will detect only light having wavelengths between 584 and 601 nm, corresponding to object planes between Z5+25 microns and Z5+37.5 microns; and camera pixels lying directly behind pixel type 206 will detect only light having wavelengths between 601 and 618 nm, corresponding to object planes between Z5+37.5 microns and Z6 (i.e., Z5+50 microns).

Referring now to FIG. 7B, a first viewing angle for a hyperchromatic optical tomography system incorporating a long depth of field is schematically illustrated. The components comprising the system are similar to those of FIG. 6B, except that a mechanical translator for the objective lens, such as a PZT, is no longer necessary. The ray paths 405 and 406 originate at opposite sides of the tube 205 and follow similar paths to the image sensor 104 at focus point A". A CFA 201 is also shown, although it is optional in this embodiment.

Referring now to FIG. 7C, there schematically illustrated is the object space for a second viewing angle for a hyperchromatic optical tomography system incorporating a long depth of field. Here the cell 144 is rotated to a second viewing angle of $\theta_2$. Because the cell 114 is always within the boundaries of the extended depth of field (i.e., between planes Z5 and Z6), it is not necessary to employ a PZT to move the objective lens 103.

Figure 7D:
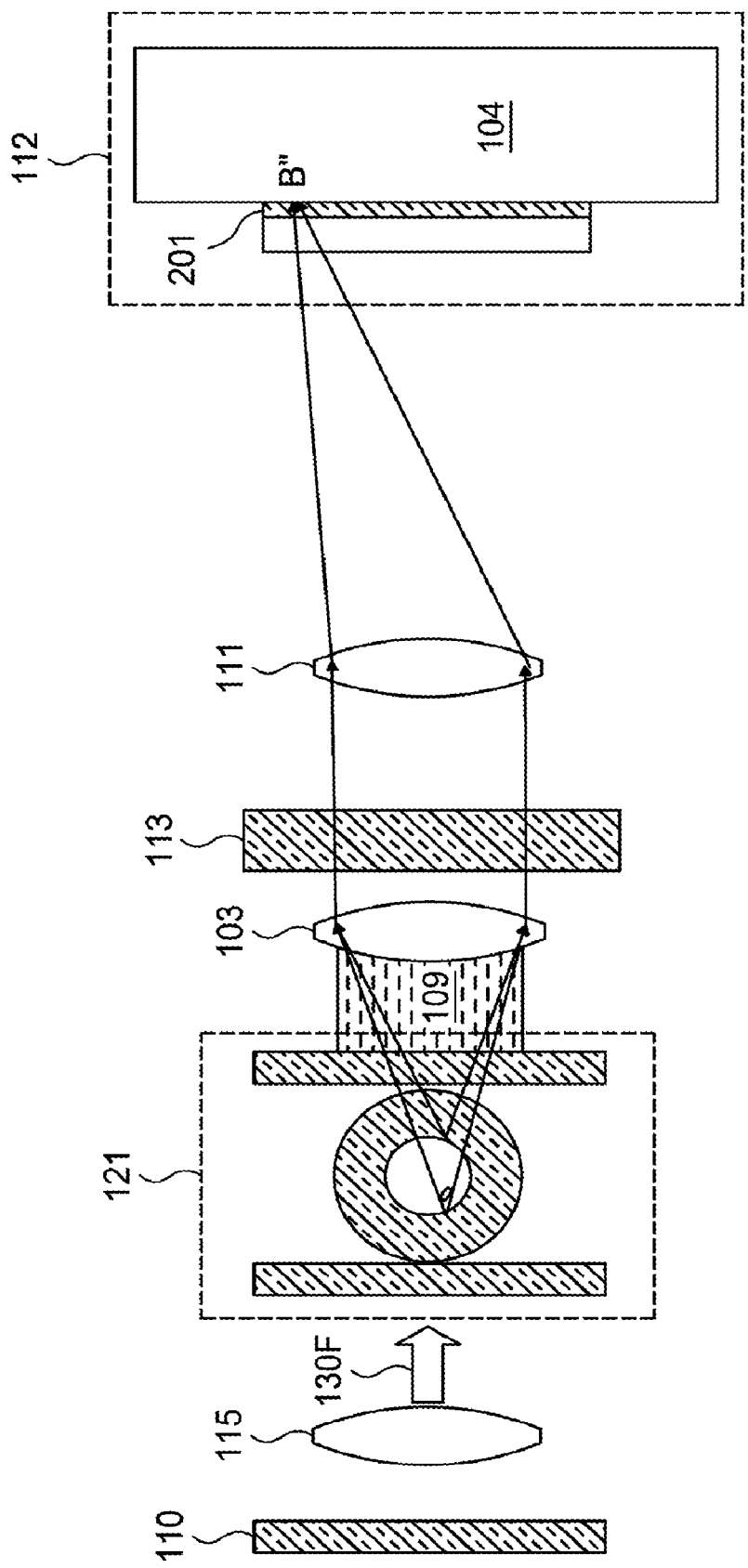
FIG. 7D schematically illustrates a second viewing angle for a hyperchromatic optical tomography system incorporating a long depth of field.

Referring now to FIG. 7D, a second viewing angle for a hyperchromatic optical tomography system incorporating a long depth of field is schematically illustrated showing the system detailed in FIG. 7C. In contrast to FIG. 7B, it should be noted that the focus of objective 103 has shifted to focus point B" on image plane 104. A CFA 201 is also shown, although it is optional in this embodiment.

Figure 8A:
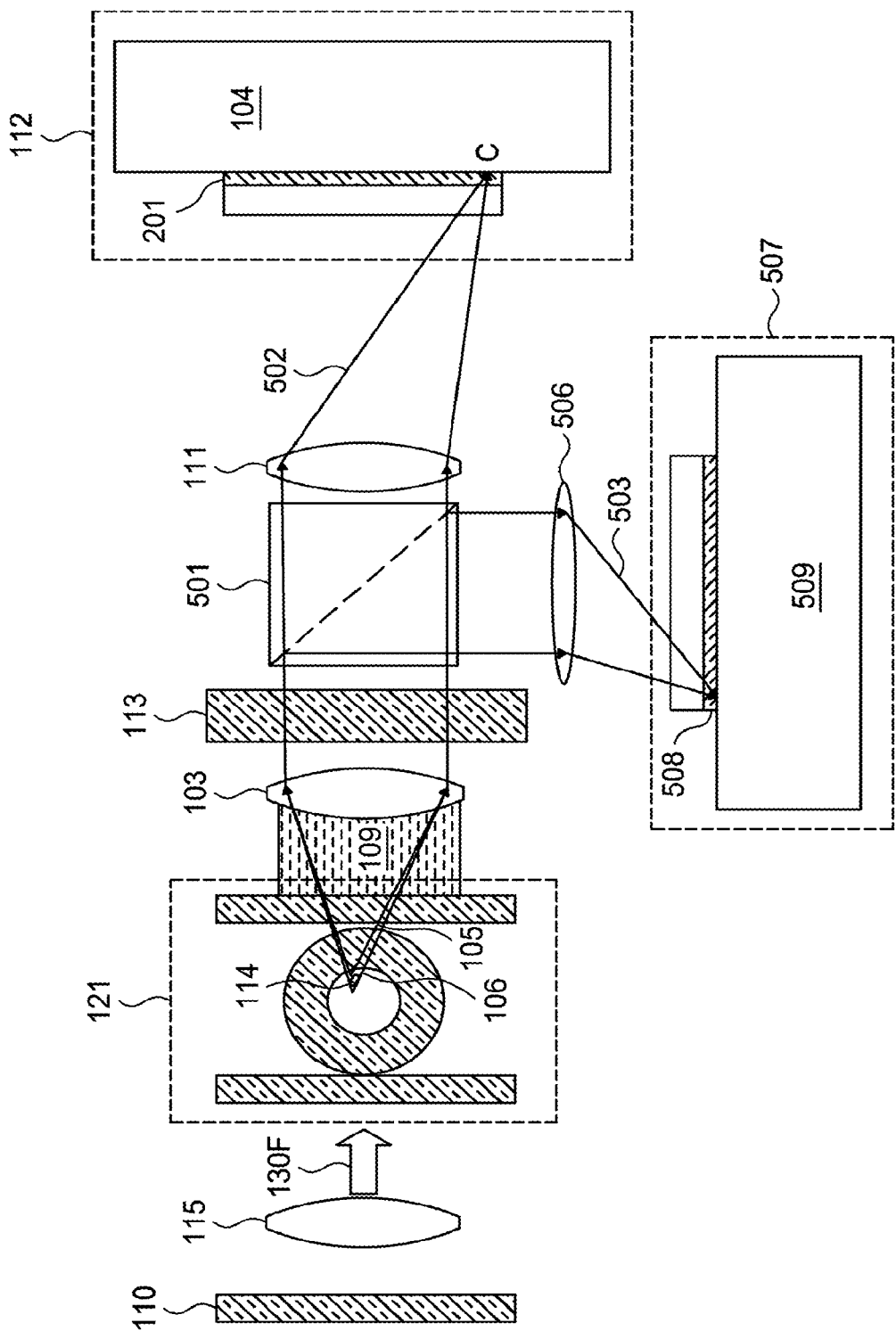
FIG. 8A schematically illustrates a first viewing angle for a hyperchromatic optical tomography system incorporating multiple detection paths.

Referring now to FIG. 8A, an example of multiple camera system where a capillary tube holding a specimen is at a first rotation angle is shown. A multiple camera system includes a chromatic filter 110 and a condenser lens 115, and a tube assembly 121, containing, for example, a biological cell 114 substantially as described hereinabove with reference to FIG. 4A and FIG. 4B. Ray paths beginning near the cell 114 at object planes Z1 and Z2, respectively, pass through the immersion fluid 109 and the hyperchromatic objective lens system 103. In a departure from the system described above with reference to FIG. 4A and FIG. 4B, the multiple camera system here incorporates a dichroic beamsplitter cube 501 to split a first plurality of ray paths 502 and 503. The first plurality of ray paths 502 and 503 originate in object planes similar to object planes Z1 and Z2. Each camera may optionally be filtered by a chromatic filter array 201, 508. In an alternate embodiment, a polarization filter array may be substituted for each chromatic filter array. If a wide depth of field is desired, then another embodiment, similar to this one, would employ CFAs 201 and 508 while eliminating the translational mechanism 113 for moving the objective lens similarly to other embodiments described above.

Figure 8B:
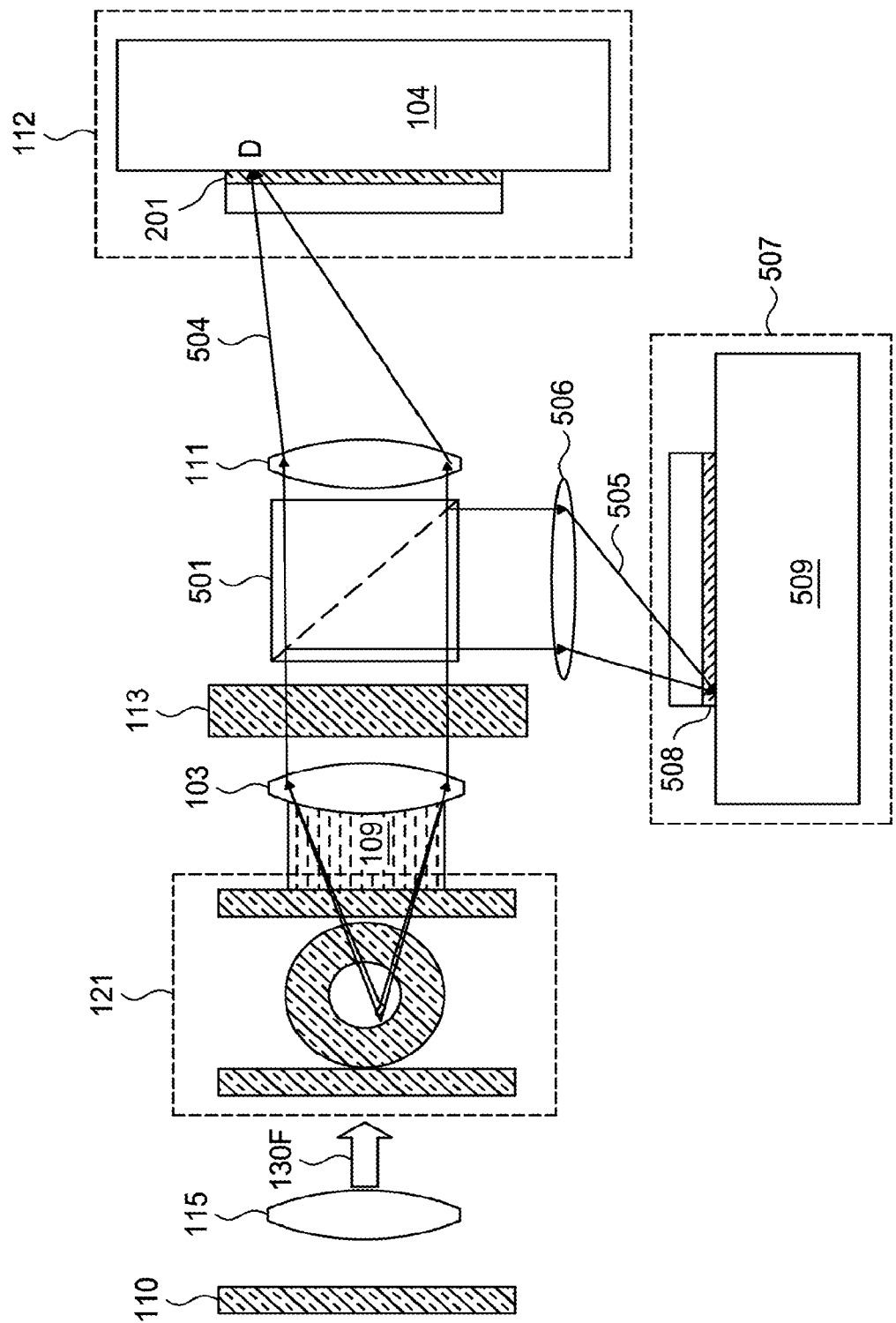
FIG. 8B schematically illustrates a second viewing angle for a hyperchromatic optical tomography system incorporating multiple detection paths.

Referring now to FIG. 8B, an example of the multiple camera system of FIG. 8A where the capillary tube holding a specimen is at a second rotation angle is shown. Here the dichroic beamsplitter cube 501 splits a second plurality of ray paths 504 and 505. The second plurality of ray paths 504 and 505 originate in object planes similar to object planes Z3 and Z4.

Referring now jointly to FIG. 8A and FIG. 8B, the rays 502 and 504, being of the same wavelength, travel through the first tube lens 111 to the first camera 112. The rays 503 and 505, being of a wavelength different from rays 502 and 504, travel through the second tube lens 506 to the sensor area 509 of a second camera 507. Additional dichroic beamsplitters and cameras may be readily envisaged.

Focus Score

One characteristic of an OPTM system incorporating extended depth of field optics is that a fixed-focal plane image can no longer be acquired through the extended depth of field optical path. The focus quality of a flat object is retained over a wide range of focal positions. This property is sometimes referred to as focus invariance.

For an object that is not confined to a single focal plane, it is still necessary to find the midpoint of the object of interest so that it may be kept within the focus interval throughout the data acquisition. One method of accomplishing this is to split the optical path prior to introducing the chromatic aberration, so that a separate optical path, incorporating a detector, is available. This separate optical path, being free of chromatic aberration, allows the system to acquire fixed-focal plane images. In a similar method that can be incorporated into a hyperchromatic imaging system, the optical path can be split and one arm chromatically filtered to near-monochromaticity, so that a single focal plane can be imaged by a separate camera, while the other arm provides the pseudo-projection. Another approach includes panning the objective lens over a wide range prior to beginning the scan, acquiring an image at each position, and assigning a focus score to each image. Focus scoring methods may employ autocorrelation, entropy, and/or other equivalent methods.

Figure 9:
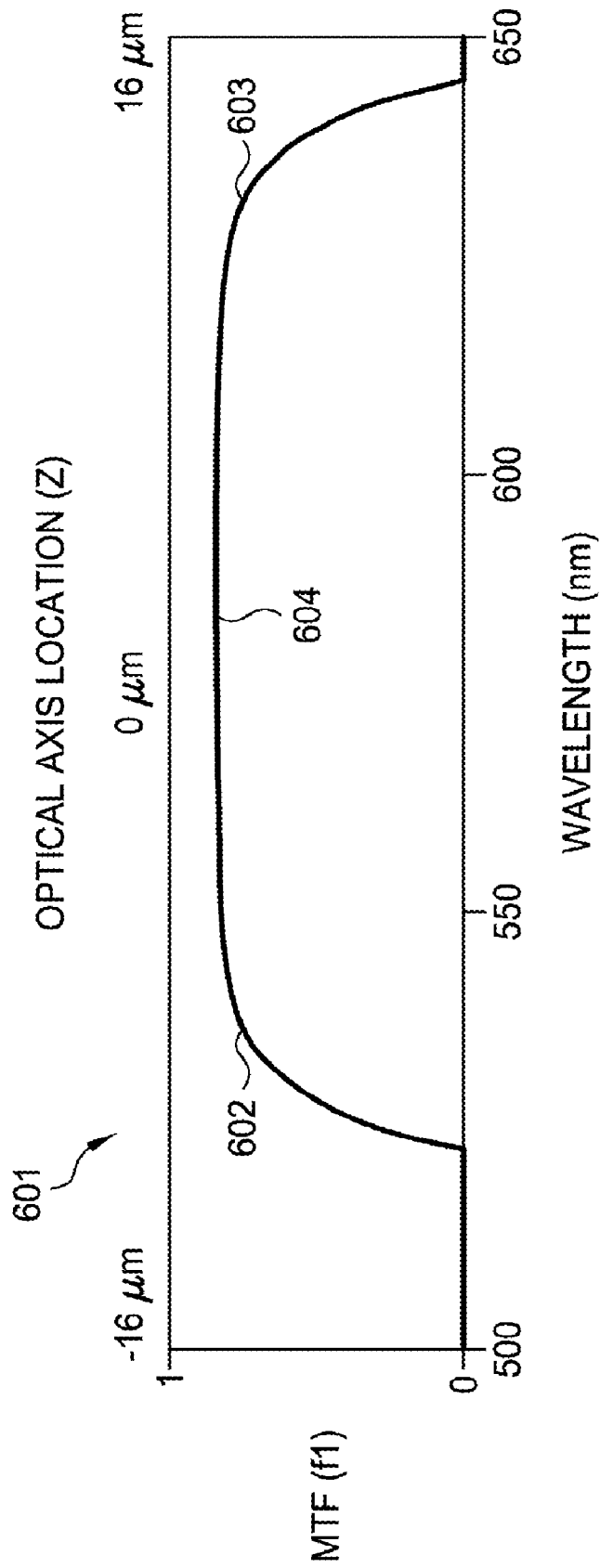
FIG. 9 illustrates an example of focus invariance in an MTF range.

Referring now to FIG. 9, an example of focus invariance in an MTF range is illustrated. A focus-invariant range for the MTF at one spatial frequency, MTF (f1) 601 is bounded on the optical axis by an upper focal plane 602 and a lower focal plane 603. Within these boundaries the MTF 601 remains at a roughly constant plateau value before dropping down to a much lower level. Using such an approach, as described further below, the two end-points of the plateau 602, 603 in the MTF (f1) 601 can be identified, and the preferred focus chosen by, for example, the mid-point 604 between the end-points 602, 603.

Repetitive focus scoring is not necessary for a system having a depth of field exceeding the inner diameter of a microcapillary tube, provided that the upper and lower boundaries 602, 603 of the focus invariance region do not pass through the interior of the microcapillary tube. This condition can be verified by an initial focus scoring when the instrument is first configured.

Figure 10:
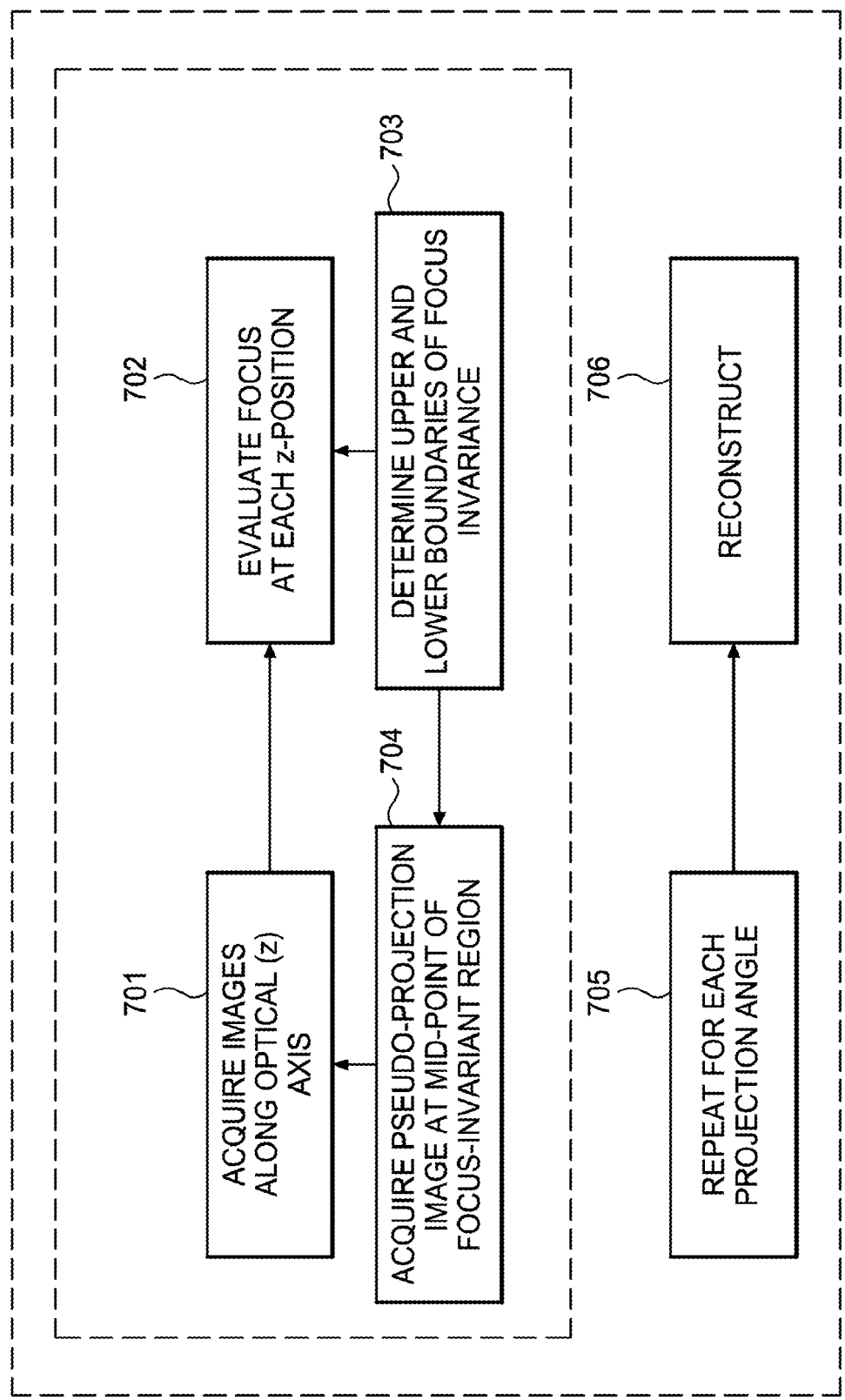
FIG. 10 shows a block diagram of a method for finding the midpoint of the focus-invariant region in a focus-invariant optical tomography system.

Referring now to FIG. 10, a block diagram of an example method for finding the midpoint of the focus-invariant region in a focus-invariant optical tomography system is schematically shown. According to the example method the midpoint is found and used to compute a 3D reconstruction of an object by:

1. panning through the optical axis and acquiring multiple images of an object in a microcapillary tube while panning (701);
2. evaluating the focus quality at each position along the optical axis (702);
3. determining two break points on the optical axis where the focus quality begins to degrade (703), where the two break points correspond to the upper and lower boundaries 602, 603 of the focus invariance region;
4. acquiring a pseudo-projection image (704), with the center of the pseudo-projection's scanning range centered between the upper and lower boundaries 602, 603 of the focus invariance region;
5. rotating the microcapillary tube to a next projection angle;
6. repeating steps 1-5 until a plurality of pseudo-projections have been acquired at a plurality of projection angles (705);
7. computing a 3D reconstruction using the acquired pseudo-projections (706).

Figure 11A:
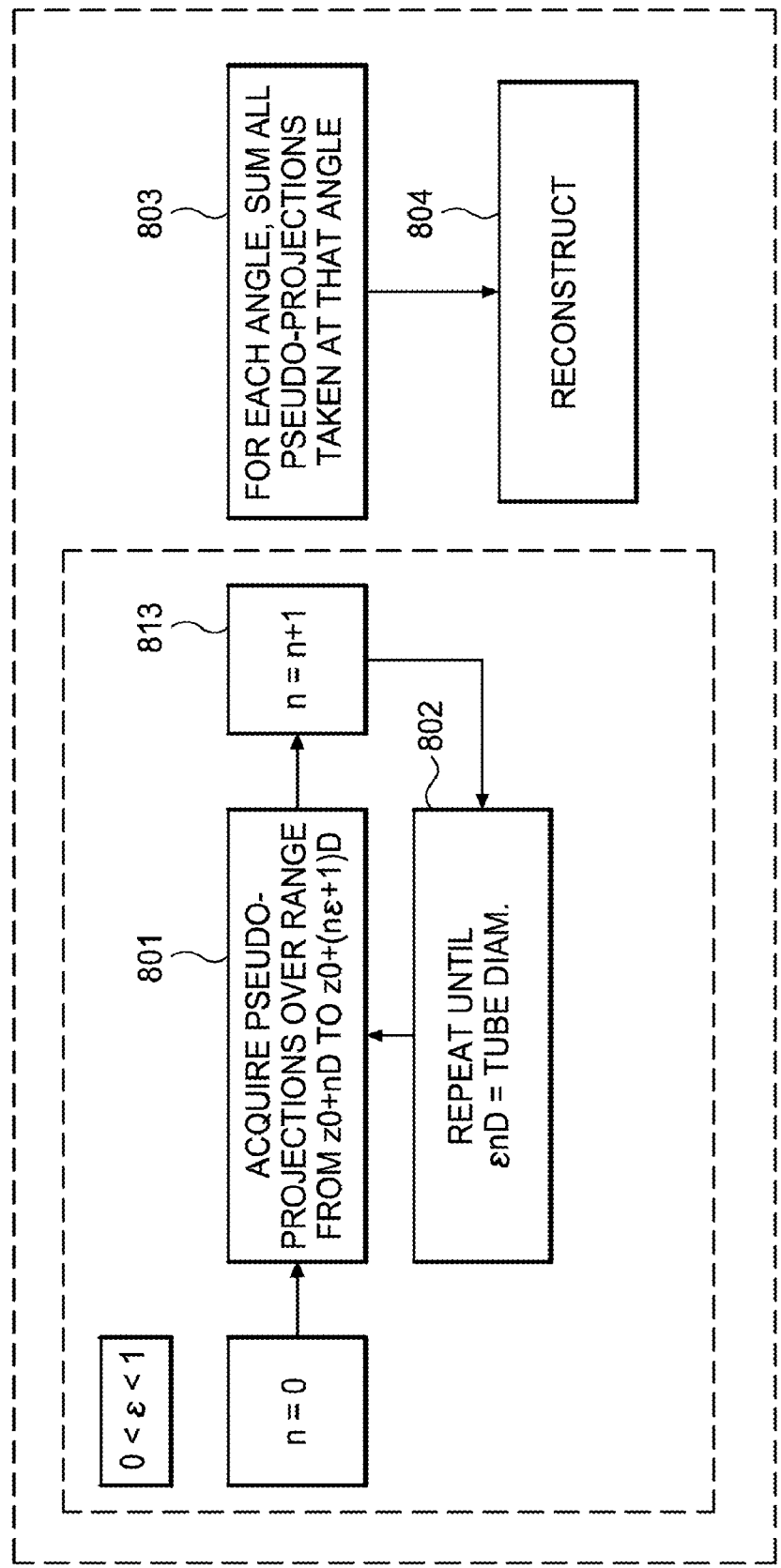
FIG. 11A shows a block diagram of another method for finding the midpoint of the focus-invariant region in a focus-invariant optical tomography system.

Referring now to FIG. 11A, a block diagram of another method for finding the midpoint of the focus-invariant region in a focus-invariant optical tomography system is shown. According to this alternate example method the midpoint is found and used to compute a 3D reconstruction of an object by:

1. for a first viewing angle, acquiring pseudo-projections at a plurality of focal planes 801 by stepping the focus (i.e. by moving the objective lens a short distance represented by n=n+1, where n is an incremental step) and acquiring pseudo-projection data at each focal plane 813;
2. moving to a next viewing angle and repeating the acquisition of pseudo-projections 801 until a target volume is covered by stepping the focus as above 802;
3. summing all pseudo-projections for each viewing angle 803 to produce a set of summed pseudo-projections; and
4. computing a 3D reconstruction using the set of summed pseudo-projections 804.

In one example, pseudo-projections are acquired until the following formula is met or exceeded at 802:

$$\epsilon nD = \text{tube diam, where } 0 < \epsilon < 1.$$

Figure 11B:
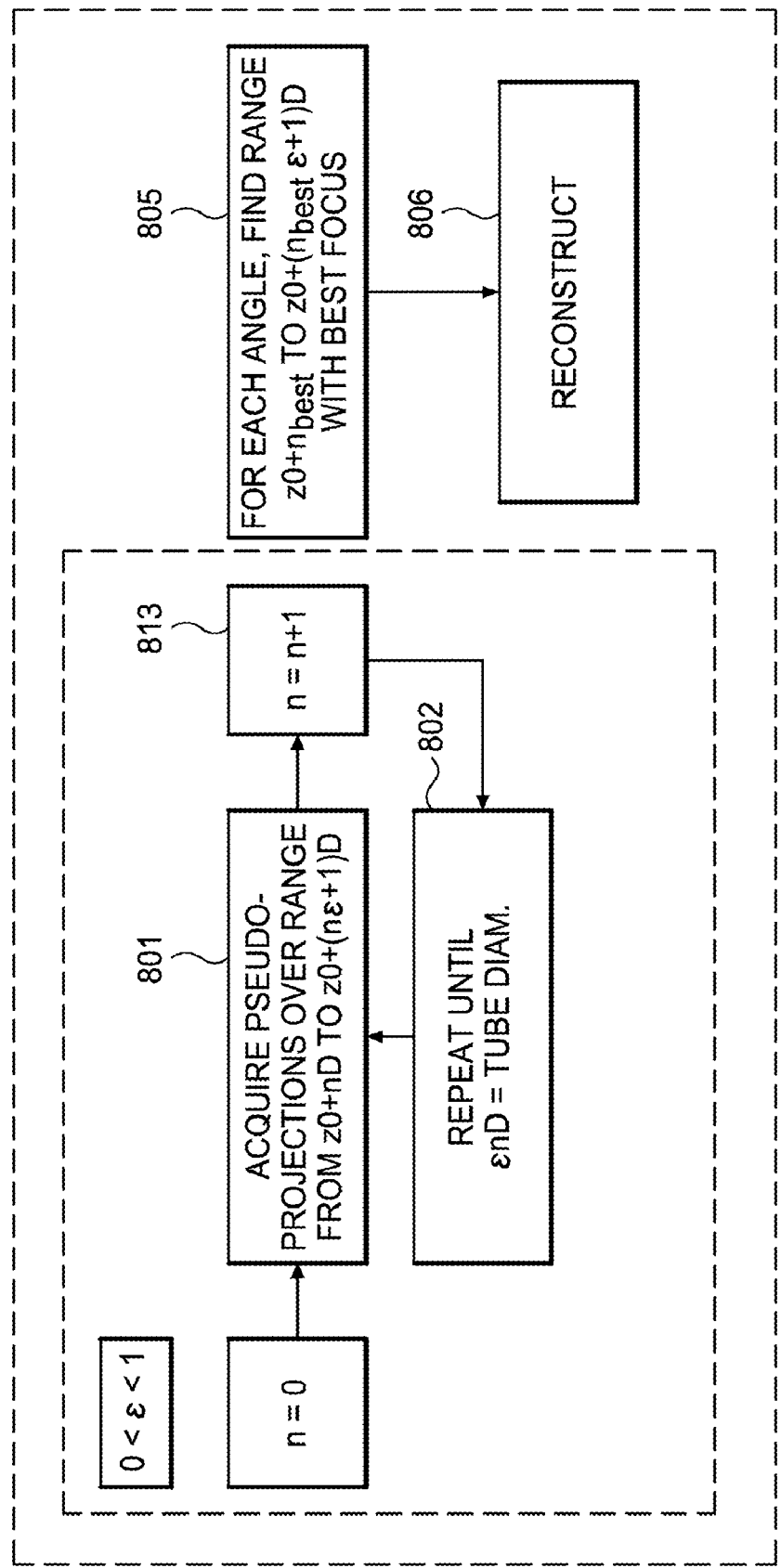
FIG. 11B shows a block diagram of yet another method for finding the midpoint of the focus-invariant region in a focus-invariant optical tomography system.

Referring now to FIG. 11B shows a block diagram of yet another method for finding the midpoint of the focus-invariant region in a focus-invariant optical tomography system. According to this alternate example method the midpoint is found and used to compute a 3D reconstruction of an object by:

1. for a first viewing angle, acquiring pseudo-projections at a plurality of focal planes 801 by stepping the focus (i.e. by moving the objective lens a short distance represented by n=n+1, where n is an incremental step) and acquiring pseudo-projection data at each focal plane 813;
2. moving to a next viewing angle and repeating the acquisition of pseudo-projections 801 until a target volume is covered 802 by stepping the focus as above 802 according to a limiting formula;
3. performing a 2.5-D focus evaluation 805 to determine a best focus pseudo-projection for each viewing angle; and
4. computing a 3D reconstruction using a set of best focus pseudo-projections acquired at the best focus for each angle 806.

The method above is similar to that of FIG. 11A except for the 2.5-D focus evaluation.

Figure 12:
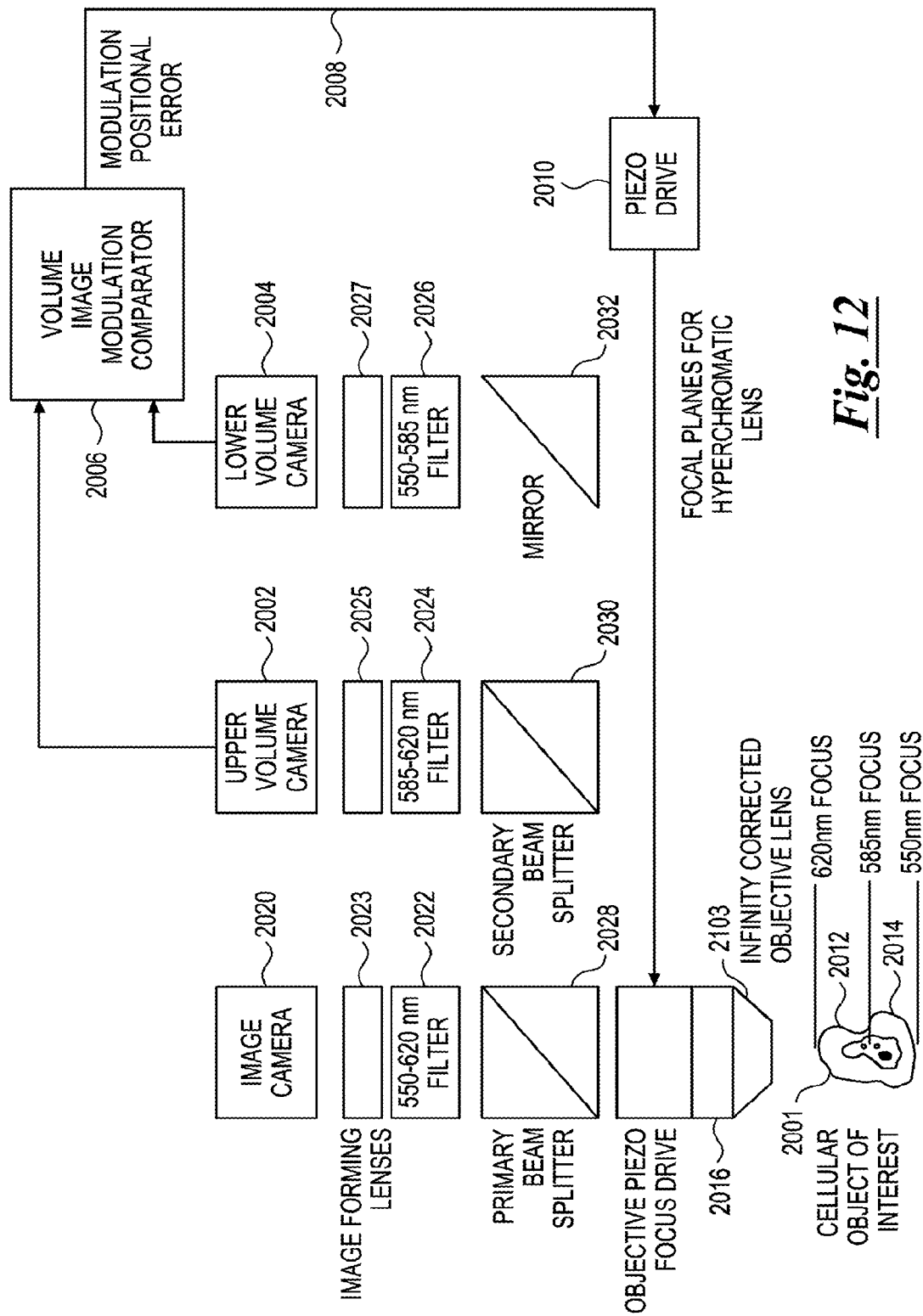
FIG. 12 schematically depicts an embodiment of an autofocusing system using chromatic balance.

Referring now to FIG. 12, an embodiment of an autofocusing system using chromatic balance is schematically shown. Here two autofocusing cameras 2002, 2004 provide digitized input to an image comparator 2006, which in turn provides a feedback signal 2008 to a transducer drive 2010, such as a PZT controller. As an object of interest 2001 is rotated within a microcapillary tube (as described above), separate images from an upper object volume 2012 and a lower object volume are captured by the autofocusing cameras 2002, 2004. The images are compared and analyzed by the comparator 2006. The feedback signal 2008 from the comparator 2006 drives the transducer drive 2010 which, in turn, controls an objective lens focus drive 2016 so that the focus range of an objective lens 2103 moves closer to the region of poorer focus quality. When the difference in focus quality between the two images becomes sufficiently small, the transducer drive is no longer required for shifting the focus range. This process can be repeated for each projection angle, which may be necessary as the planes containing the object of interest move up and down the optical axis as the tube rotates. Images are acquired by an image camera 2020.

In one embodiment, light rays are directed by a primary beam splitter 2028, a secondary beam splitter 2030 and a mirror 2032. Light rays directed to the image camera 2020 are filtered by a first filter 2022, where the first filter passes light having wavelengths between 550 nm and 620 nm through a first image forming lens 2023. Light rays directed to the first autofocusing camera 2002 are filtered by a second filter 2024, where the second filter passes light having wavelengths between 585 nm and 620 nm through a second imaging lens 2025. Light rays impinging mirror 2032 are directed to the second autofocusing camera 2004 after being filtered by a third filter 2026, where the third filter passes light having wavelengths between 550 nm and 585 nm through a third imaging lens 2027.

Figure 13:
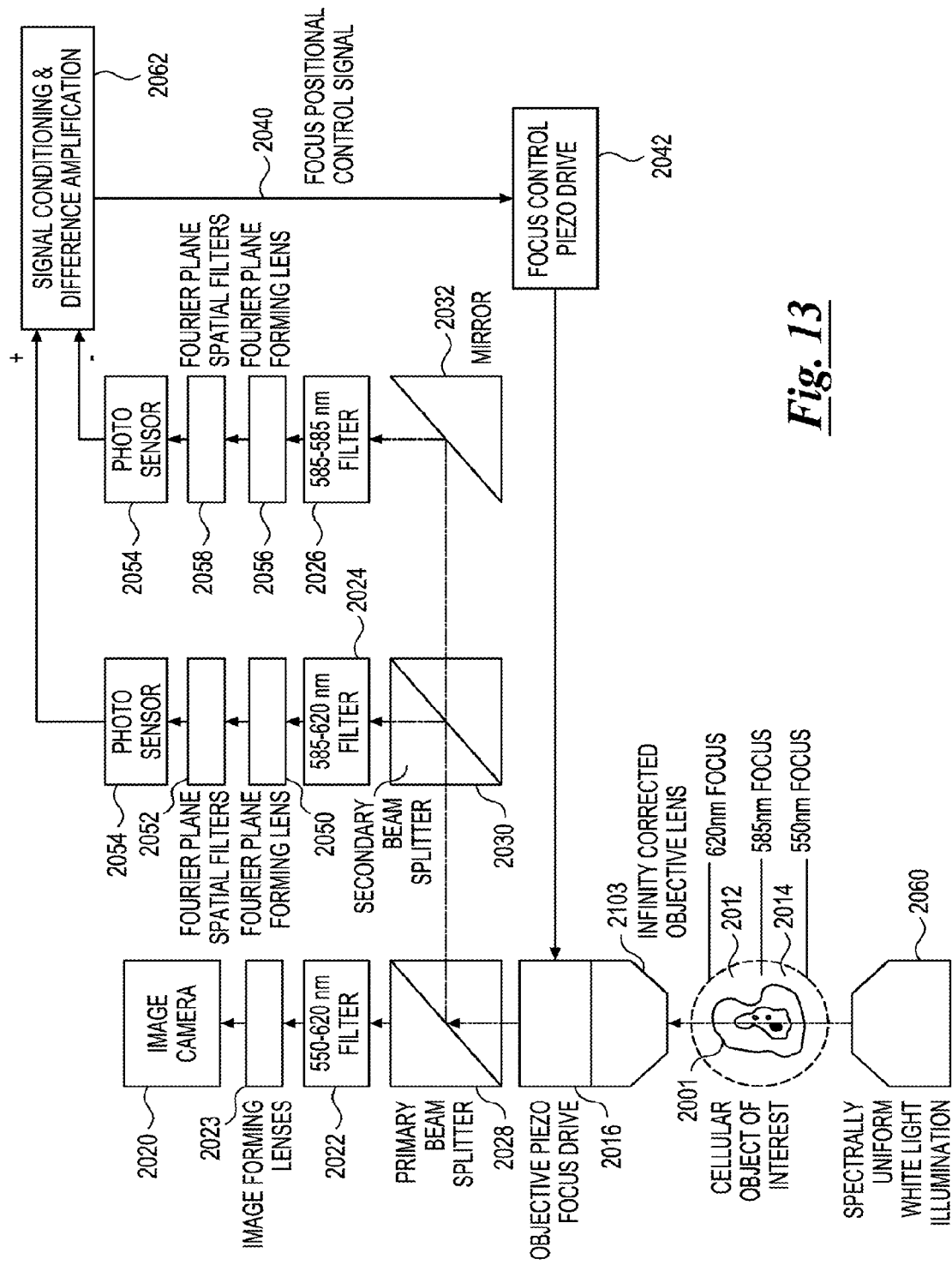
FIG. 13 shows another method for finding the midpoint of the focus-invariant region in a focus-invariant optical tomography system, using two photo-diodes with spatial-frequency filtering.

Referring now to FIG. 13, another embodiment of an autofocusing system using chromatic balance is schematically shown. A source of spectrally uniform light illumination 2060 illuminates an object of interest 2001 which is imaged by image camera 2020. Similarly to the autofocusing system described above, light rays are directed by a primary beam splitter 2028, a secondary beam splitter 2030 and a mirror 2032. Light rays directed to the image camera 2020 are filtered by a first filter 2022, where the first filter passes light having wavelengths between 550 nm and 620 nm through a first image forming lens 2023. A portion of light rays passing through the secondary beam splitter 2028 are filtered by a second filter 2024, where the second filter passes light having wavelengths between 585 nm and 620 nm. Light rays impinging mirror 2032 are filtered by a third filter 2026, where the third filter passes light having wavelengths between 550 nm and 585 nm. A first Fourier plane forming lens 2050 transmits light from the second filter 2024 through a first Fourier plane spatial filter 2052 to a first photo sensor 2054. A second Fourier plane forming lens 2056 transmits light from the third filter 2026 through a second Fourier plane spatial filter 2058 to a second photo sensor 2054.

The Fourier spatial filters 2052, 2058 operate on two focus paths to provide analog feedback to the focus control controller 2042 via the photo-diodes 2054. Spatial filtering ensures that the photodiodes only receive the high-spatial frequency components of a focal plane. High spatial frequency content is associated with well-focused objects. The high frequency content of the upper and lower halves of the focal range, 2012, 2014 respectively, is compared in signal conditioning and difference amplification processor 2062. The difference amplification processor 2062 provides output 2040 which is used as above to control drive 2042 to cause the transducer 2016 to position the objective lens 2103 until the high-frequency intensities of the two focal regions are sufficiently similar. Under continuous illumination, this method has the advantage of tracking motion of an object keeping it in focus balance at all times.

Polarization-Dependent Optics (Birefringent) for 3D Imaging

The location of the focal plane is dependent on the polarization of the light. This system can be implemented using birefringent optics, in which the index of refraction varies according to the electric-field polarization of the optical wavefront. An example of a birefringent optical material is calcite ($CaCO_3$), for which the index of refraction at 590 nm is either 1.658 or 1.486, depending on the polarization.

Embodiments analogous to those of the hyperchromatic systems described above may be employed. With these techniques, the polarization of the imaged light will depend on the object focal plane from which it originated. For example, the horizontally-polarized (electric-field vector at zero degrees) component of the light may provide the in-focus image for an object plane $Z_H$, whereas the vertically-polarized (electric-field vector at 90 degrees) component of the light may provide the in-focus image for an object plane $Z_V$, located, for example, 15 microns closer to the detector than plane $Z_H$. Light having polarizations between zero and 90 degrees would provide in-focus images for object planes between $Z_H$ and $Z_V$.

The polarization of the illuminating light can be varied over time by using a spinning polarizing filter, the collected (unpolarized) light passes through a polarizing filter before it reaches the image sensor, or the entire focal range can be collected simultaneously.

In one embodiment, the focal range may be comparable to the thickness of the object, e.g., 15 microns. In this embodiment, a PZT can be incorporated to compensate for rotation-induced translation of the cell, in a system analogous to that depicted in FIG. 6A and FIG. 6B.

In another embodiment, analogous to that depicted in FIG. 7A-FIG. 7D, the range of the focal planes can be equivalent to the diameter of the microcapillary tube (e.g., 50 microns), and a Polarization Filter Array (PFA; the polarization analog of the chromatic filter array illustrated in FIG. 5) is incorporated into the system in place of the CFA shown in FIG. 7A-FIG. 7D.

In yet another embodiment, the range of the focal planes can be equivalent to the diameter of the microcapillary tube, and the polarization of the light varied over time while a series of synchronized camera exposures acquires the object planes as they come into focus on the detector.

2.5-D Imaging

In any OPTM system incorporating extended depth of field optics, post-acquisition processing may be incorporated to perform pixel-by-pixel analysis to compute a mosaic of in-focus features in the field of view. An example of one type of 2.5-D imaging is found in R J Pieper and A Korpel, "Image processing for extended depth of field," *Applied Optics* 22, 1449 (1983). The 2.5-D imaging approach may be most advantageously employed in those embodiments that make use of a Chromatic or Polarization Filter Array (CFA or PFA) and covering a wide focal range, and in the embodiments that make use of multiple camera exposures. In these systems, the weight assigned to an element type can vary from one pseudo-projection to the next, as the object is rotated through different focal plane regions.

To accomplish this, individual features are identified in the collection of short-focal-plane images that form an image stack. The same feature may appear in several images within the stack, but only a subset of those images will contain a well-focused representation of that feature.

Figure 14:
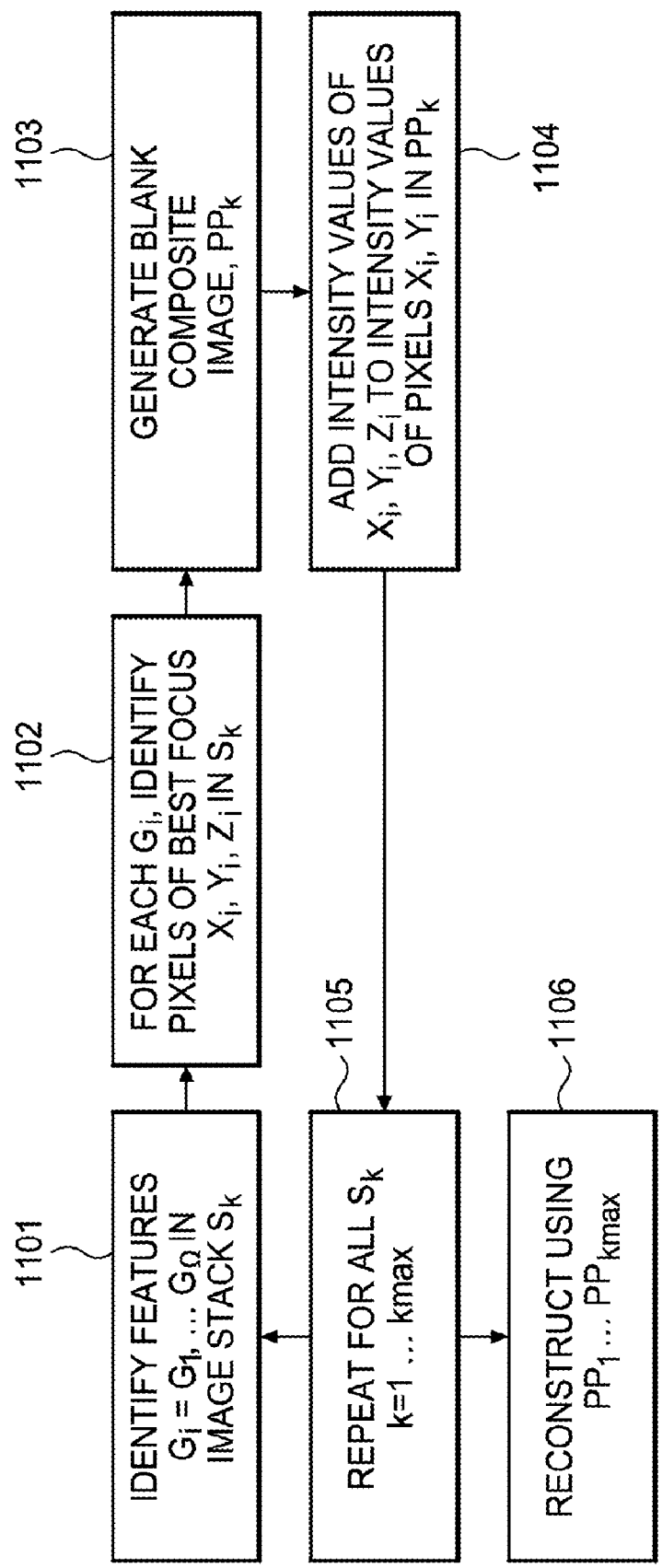
FIG. 14 schematically shows a block diagram of a method for 2.5-D imaging in a focus-invariant optical tomography system.

Referring now to FIG. 14, a block diagram of a 2.5-D focusing method is schematically shown. Features, $G_i = G_1, \ldots G_\Omega$ in an image stack $S_k$ are identified 1101. For each feature $G_i$ in an image stack $S_k$, the images for which $G_i$ is in best focus are identified 1102. A blank composite image $PP_k$ is generated 1103. The pixels that make up that best-focused feature $(X_i, Y_i, Z_i)$ are added to the composite image $PP_k$ 1104. This process is repeated for all features ($G_1, G_2 \ldots G_\Omega$) until all features have been incorporated into $PP_k$. Since a single feature may span two or more images in $S_k$, a single pixel in $PP_k$ may accumulate two or more intensity values, one for each image in $S_k$ that contains a well-focused representation of $G_l$. Furthermore, two or more features may share the same X-Y coordinates (but different Z-coordinates), which may result in some pixels in $PP_k$ accumulate intensity values from two or more features. Note that subscripted letters l,k etc. represent index numbers.

The process is repeated for all the image stacks, until all image stacks $(S_1) S_2 \ldots S_{kmax})$ have been analyzed and their associated composite images $(PP_1, PP_2 \ldots PP_{kmax})$ have been computed 1105. The tomographic reconstruction can then be computed, using the set of $PP_k$ as the input images 1106. In one example using this method, each 2×2 block of a 4-color CFA or PFA can be processed by selecting the single pixels containing the best focus, or as a weighted sum of two or more pixels.

Beam Split Multiple Focal Plane

There are several fundamental advantages of shorter integrated pseudo-projections for OPTM performance. First, smaller magnitude pseudo-projections (integrated optical axis scans) reduce the effect of the low frequency information dominating in the spatial spectrum. Second, adding more images that sample the same volume improves the signal to noise proportionally to the square root of the number of images used. Third, multiple images enable the detection and compensation for unusual hot spots in images due to refractive contrast.

The separation of the depth of field into segments allows many other depth of field extenders to work to supply a more limited solution, working better with less complication.

A reduced range of motion or an extended depth is possible with direct objective scan and multiple camera focal planes.

The creation of multiple focal ranges does not necessarily require multiple cameras. With adequate camera sensor area it is possible to merge the images and capture them on a single sensor. This can be done using a fiber optic faceplate splitting the sensor into zones, or a folded optical system merging the multiple images onto a single CCD.

Figure 15:
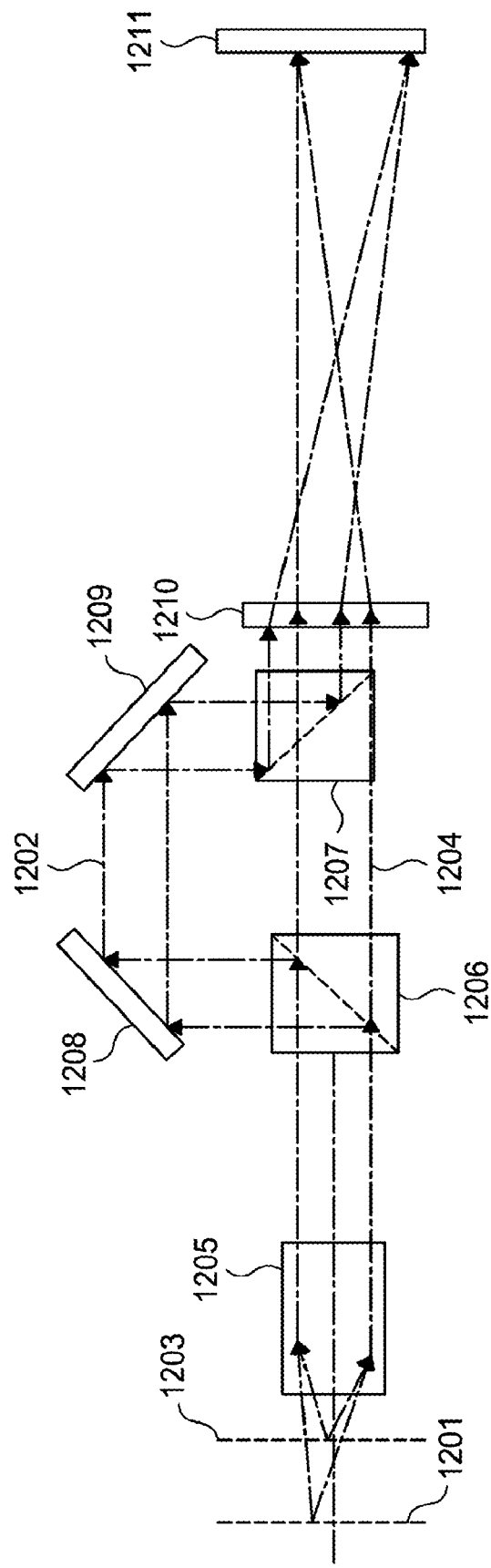
FIG. 15 illustrates an example of a folded optical system allowing simultaneous imaging of two focal planes on a single camera.

Referring now to FIG. 15, an example of a folded system is depicted. The substantially collimated light exiting the objective 1205 is divided by a first dichroic beam-splitting cube 1206. One arm 1202 has a wavelength λ1 and originates in a first focal plane 1201. It passes through a first tube lens, through a second beam-splitter cube 1207, and onto the right half of the camera sensor's active area 1211. The other arm 1204 has a wavelength λ2 and originates in a second focal plane 1203. It reflects off two mirrors 1208, 1209, passes through the tube lens 1210, reflects within the second dichroic beam-splitter cube 1207, and onto the left half of the camera sensor's active area 1211. The two halves of the camera will acquire focused images having substantially identical magnifications, but originating from different focal planes 1201, 1203 in object space. The relative lateral shift in the images is achieved by laterally shifting the second dichroic beam-splitter cube 1207, so that the reflected light of the second arm 1204 is laterally shifted relative to the first arm 1202 and to the tube lens 1210.

Two-Stage Magnification

Acquiring images separated by 10 microns in object space would require, for a 100× lens, a difference in image-space path length proportional to magnification squared (i.e., 100 mm). If the tube lenses have the same focal lengths, but different back focal planes, then the two halves of the camera will acquire focused images having substantially identical magnifications, but originating from different focal planes in object space. As an illustration, placing the camera 100 mm closer to the second tube lens than to the first tube lens will result in a difference in focal planes of $100/m^2$ microns, where M is the lateral magnification. If M=100, then $100/m^2$=10 microns.

However, a much more modest change in optical axis can be achieved using two 10× magnification stages and changing the focal plane of the secondary objective only slightly. A 10-micron shift in the specimen plane at 10× magnification image is achieved with a one-millimeter shift of the intermediate image plane.

Figure 16:
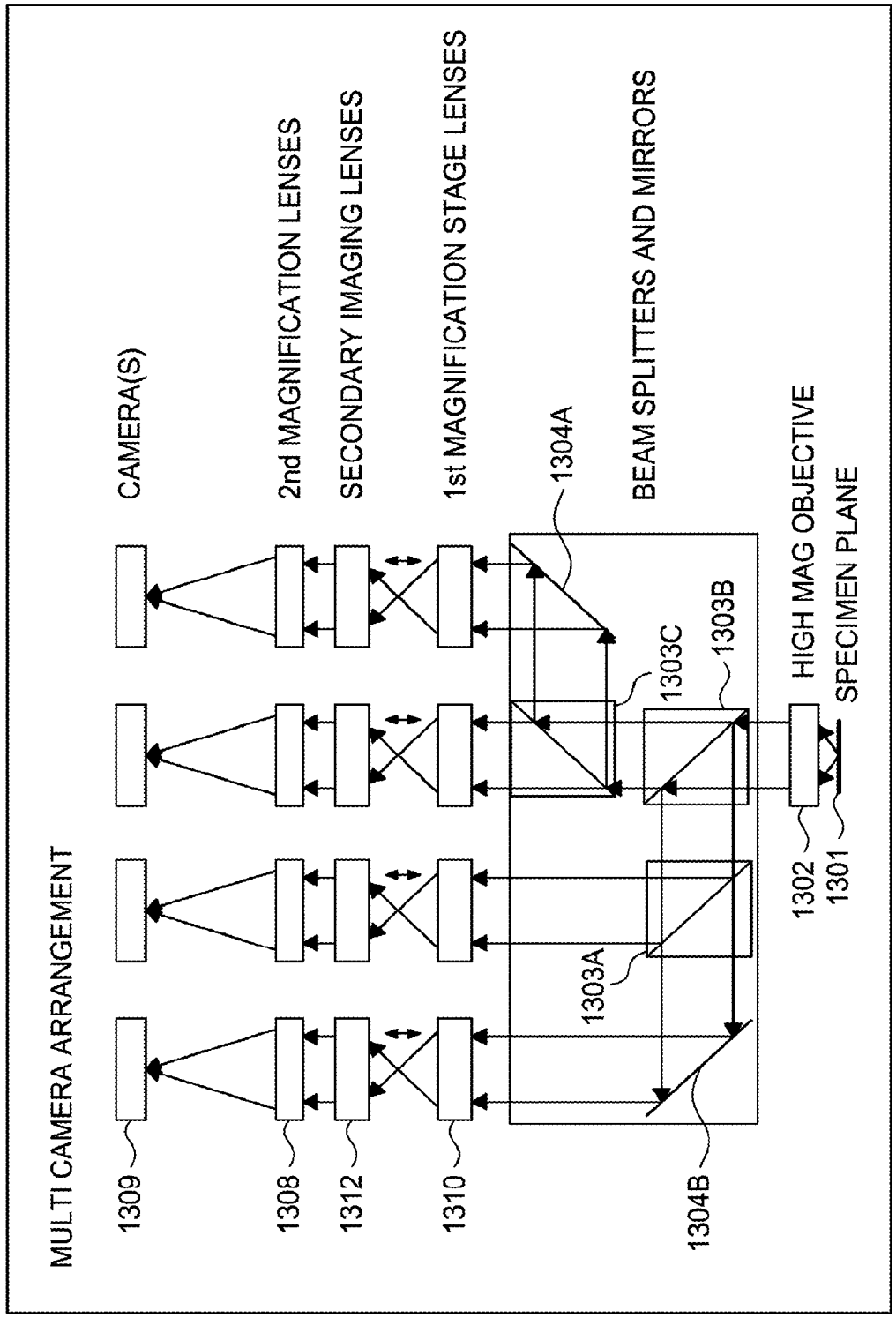
FIG. 16 schematically illustrates a multiple-camera device for acquiring a range of focal planes in an optical tomography system.

Using a split focal plane approach allows two or more cameras (four are shown in the example of FIG. 16) to each collect a range of the focal depth of the specimen. In the limit the number of cameras is practically limited by the amount of light that can be brought to illuminate the specimen and the cost and complexity of the optical path. A system incorporating more cameras improves signal to noise, assuming that the cameras' well capacities are sufficiently close to full, and reduces the range that each image must deliver in field depth. A shorter field depth aids in producing better representation of high spatial frequencies in a resultant pseudo-projection.

In an example of this embodiment, shown in FIG. 16, an optical system comprises a primary objective 1302, first and second mirrors 1304A, 13048, three beam-splitters 1303A-1303C, four primary tube lenses 1310, four secondary objective lenses 1312, four secondary tube lenses 1308, and four CCD cameras 1309. The primary objective 1302 and the primary tube lenses 1310 provide at least 10× magnification, and the secondary objectives and tube lenses provide at least an additional 10× magnification, for a total of at least 100× magnification.

Each ray path passes through two beam-splitter thicknesses, and each ray path undergoes either two or zero reflections, either through the beam-splitters or by the mirrors. The equivalence of the ray path-lengths through the beam-splitters means that the aberrations due to passing through the glass are equivalent. The number of reflections being always even (or always odd) means that all four images retain the same orientation at the image planes of the four cameras 1309. Space between first tube lens and secondary objective differs for each ray path, so that a different object plane is focused on each camera. A reduced range of motion or an extended depth is possible with focal plane scanning behind the objective and multiple camera focal planes.

Extending the multiple camera optics to greater than 20 focal planes can, in theory, sample a ten-micron depth of field every 500 nm. The arrangement of multiple cameras allows two simultaneous modalities of volumetric sampling that can each be used to contribute their relative strengths to a more accurate volumetric reconstruction. Specifically, the contrast generated by refractive and diffractive effects in the sample media interfaces may be sorted out from the purely absorptive effects and all data captured rapidly and without focal plane motion or rotational blur.

Wavefront Coded Optics

Figure 17:
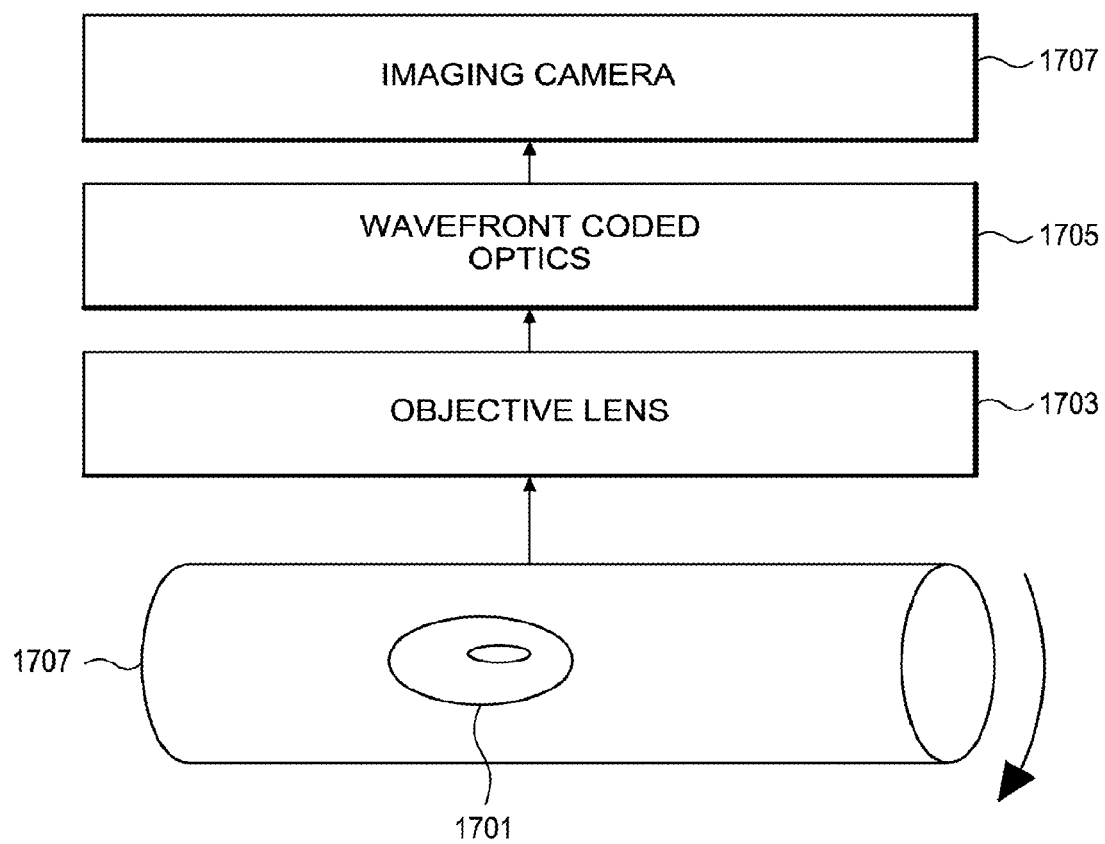
FIG. 17 illustrates a schematic diagram of an OPTM system including wavefront coded optics.

Referring now to FIG. 17, a schematic diagram of an OPTM system including wavefront coded optics is shown. As above, a microcapillary tube 1707 holds an object of interest 1701 and is rotated through various viewing angles as viewed by an objective lens 1703. Light transmitted through the objective lens 1703 impinges on wavefront coded optics 1705 which are located between the objective lens 1703 and an imaging camera 1707. The use of wavefront coded optics provides a method of pre-distorting the optical wavefront so that an object of interest is contained within an extended depth of field producing a low but consistent frequency response throughout its volume. Thus all focal planes, within a limited range along the optical axis, are equally defocused.

This constitutes the wavefront coding. Wavefront coding elements are available from CDM Optics, Inc. (Boulder, Colo.), and are described in, for example, ER Dowski, "Wavefront coding optics," U.S. Pat. No. 6,842,297 (2005).

The limit of wavefront coding is about a 12:1 improvement in the depth of field. For an optical tomography application such an improvement will provide about half of the required depth. Thus wavefront coding may advantageously be combined with one of the many other embodiments described herein to deliver a complete solution.

The point of the first contrast-reversal (MTF less than zero) occurs, for matched condenser and objective NA's, at 0.64 waves of defocus, as detailed in V N Mahajan, "Aberration Theory Made Simple" (Bellingham, Wash.: SPIE Press, 1991). This point is readily expressed in terms of the change in the optical depth, $\Delta z$, as $$\Delta z = \pm 1.28 \lambda n / (NA_{obj})^2$$

where $\lambda$ is the wavelength of the light being collected, n is the refractive index of the region between the objective lens and the object, and $NA_{obj}$ is the numerical aperture of the objective lens. For $\lambda=550$ nm, n=1, and $NA_{obj}=0.9$, this distance is $\Delta z=\pm 0.87$ microns. Then for a 12-micron-deep object, we require at least a 5× improvement in the depth of field to avoid contrast reversal at 6-micron defocus (roughly 4.4 waves of defocus).

Another embodiment of imaging with wavefront coding incorporates digital enhancement of the image with a complementary transfer function to boost the suppressed high frequency components to recover a sharply focused image while retaining the extended depth.

Another embodiment uses multiple cameras, such as is shown above, that take advantage of the wavefront coded optics approach to extended depth of field by coding each optical path with lens transfer function, thus extending the depth of field from one segment to the next. This mechanism allows for a single brief exposure such as a strobed illuminator to quickly sample a wide depth of field without mechanical motion.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices, and that various modifications, both as to the equipment details and operating procedures, may be accomplished without departing from the true spirit and scope of the present invention.

What is claimed is:

1. An optical tomography system for viewing a biological cell comprising:
    a microcapillary tube having a viewing area for positioning the biological cell;
    at least one detector;
    a motor arranged to rotate the microcapillary tube;
    means for transmitting broadband light having wavelengths between 550 nm and 620 nm into the microcapillary tube viewing area;
    a hyperchromatic lens located to receive light transmitted through the microcapillary tube viewing area; and
    a tube lens located to focus light rays transmitted through the hyperchromatic lens, such that light rays from multiple object planes in the microcapillary tube viewing area simultaneously focus on the at least one detector; wherein the hyperchromatic lens and the tube lens operate to simultaneously focus multiple object planes from the microcapillary tube viewing area on the at least one detector; wherein the biological cell is stained to impart an absorption coefficient of at least one wavelength that registers on the at least one detector; and wherein an interval spanned by the multiple object planes comprises an interval spanning the thickness of the biological cell.

2. The system of claim 1, wherein an interval spanned by the multiple object planes comprises an interval spanning the thickness of the microcapillary tube viewing area.

3. The system of claim 1, wherein the system further comprises a chromatic filter array located between the hyperchromatic lens and the at least one detector.

4. The system of claim 1, wherein the light from the multiple object planes includes light having a wavelength range of 550 nm to 620 nm spanning a focus interval of up to 50 microns.

5. The system of claim 1, further comprising a chromatic filter array located between the hyperchromatic lens and the at least one detector, so that light coming to a focus on the detector is separated into two or more wavelength bands, each wavelength band being transmitted through the chromatic filter array to a separate set of pixels on the at least one detector.

* * * * *